(12) United States Patent
Van Wyk et al.

(10) Patent No.: US 9,427,280 B2
(45) Date of Patent: *Aug. 30, 2016

(54) DUAL-MODE ELECTROSURGICAL DEVICES AND ELECTROSURGICAL METHODS USING SAME

(71) Applicant: ElectroMedical Associates LLC, Bethesda, MD (US)

(72) Inventors: Robert A. Van Wyk, St. Pete Beach, FL (US); Yuval Carmel, Rockville, MD (US); Anatoly Shkvarunets, Rockville, MD (US)

(73) Assignee: ElectroMedical Associates, LLC, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/628,427

(22) Filed: Feb. 23, 2015

(65) Prior Publication Data

US 2015/0230856 A1 Aug. 20, 2015

Related U.S. Application Data

(63) Continuation-in-part of application No. 13/572,326, filed on Aug. 10, 2012, now Pat. No. 8,992,520.

(60) Provisional application No. 61/574,821, filed on Aug. 10, 2011.

(51) Int. Cl.
*A61B 18/14* (2006.01)
*A61B 18/00* (2006.01)

(52) U.S. Cl.
CPC .. *A61B 18/1402* (2013.01); *A61B 2018/00327* (2013.01); *A61B 2018/00333* (2013.01); *A61B 2018/00529* (2013.01); *A61B 2018/00601* (2013.01); *A61B 2018/00607* (2013.01); *A61B 2018/00625* (2013.01); *A61B 2018/1412* (2013.01); *A61B 2018/1472* (2013.01); *A61B 2018/1475* (2013.01); *A61B 2217/007* (2013.01)

(58) Field of Classification Search
CPC .......... A61B 2018/00333; A61B 2018/00327; A61B 2018/00529; A61B 2018/00607; A61B 2018/00958; A61B 2018/00625; A61B 2018/00595; A61B 2018/00601; A61B 2018/00589; A61B 2018/1412; A61B 2018/1472; A61B 2018/1475; A61B 18/1402; A61B 18/1485; A61B 2218/002
USPC .............................................. 606/37, 41, 42
See application file for complete search history.

(56) References Cited

U.S. PATENT DOCUMENTS 5,318,565 A 6/1994 Kuriloff et al.
6,277,114 B1 8/2001 Bulivant et al.
(Continued)

*Primary Examiner* — Michael Peffley
*Assistant Examiner* — Thomas Giuliani
(74) *Attorney, Agent, or Firm* — Chalin A. Smith; Smith Patent LLC

(57) ABSTRACT

Herein disclosed are dual-mode electrosurgical devices designed to function in a first mode in which high-density RF energy is used to cut or vaporize tissue, and then a second mode in which lower-density RF energy desiccates tissue to produce hemostasis, as well as methods of performing electrosurgery using same. Devices formed in accordance with the principles of this invention may be used for any surgical procedure in which highly vascular tissue is cut electrosurgically in a dry or semi-dry field, examples of which include tonsillectomy, liver resection, and cosmetic procedures such as breast augmentation, breast reduction, breast mastopexy, and abdominoplasty.

20 Claims, 30 Drawing Sheets

(56) References Cited

U.S. PATENT DOCUMENTS

| | | |
|---|---|---|
| 7,364,579 B2 | 4/2008 | Mulier |
| 7,794,460 B2 | 9/2010 | Mulier |
| 8,333,761 B2 | 12/2012 | Curtis |
| 8,394,089 B2 | 3/2013 | Curtis et al. |
| 8,518,034 B2 | 8/2013 | Curtis et al. |
| 8,992,520 B2 * | 3/2015 | Van Wyk ............ A61B 18/1402 606/37 |
| 2009/0264879 A1 | 10/2009 | McClurken et al. |
| 2009/0275940 A1 * | 11/2009 | Malackowski .... A61B 18/1442 606/42 |
| 2013/0041363 A1 | 2/2013 | Van Wyk et al. |

* cited by examiner

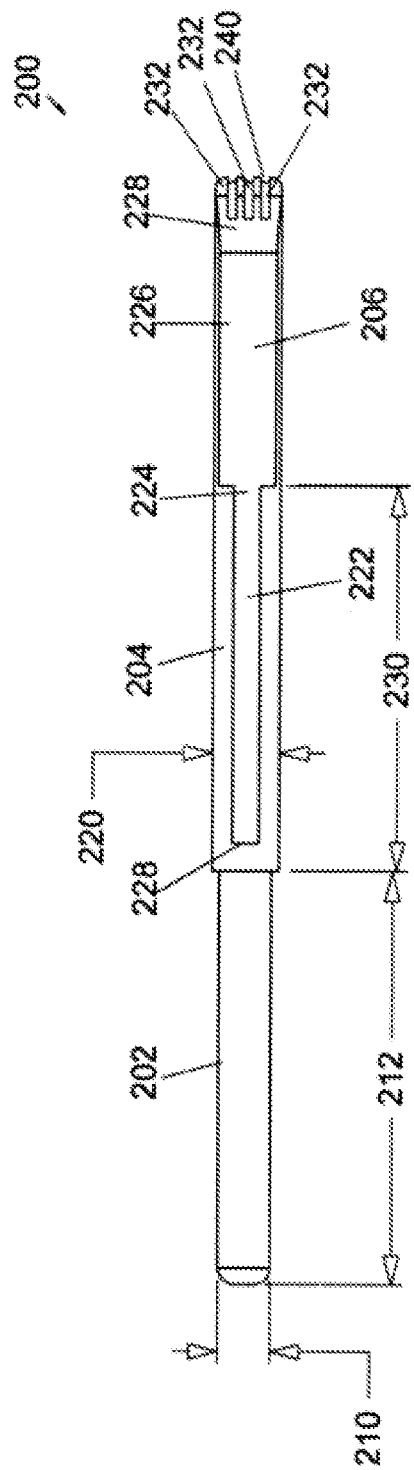
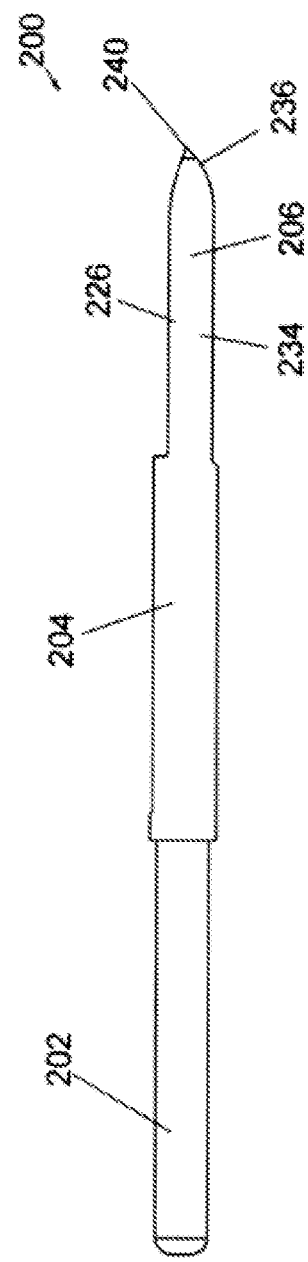

DUAL-MODE ELECTROSURGICAL DEVICES AND ELECTROSURGICAL METHODS USING SAME

PRIORITY

This application is a continuation-in-part of U.S. patent application Ser. No. 13/572,326, now U.S. Pat. No. 8,992,520, filed Aug. 10, 2012, which, in turn, claims the benefit of U.S. Provisional Application Ser. No. 61/574,821 filed Aug. 10, 2011, the entire contents of which are incorporated by reference herein.

FIELD OF THE INVENTION

The present invention relates generally to the field of medical instruments, and more particularly relates to surgical devices and methods that use radio frequency (RF) electrical energy for cutting and/or bulk removal by vaporization and coagulation with externally supplied liquid irrigants.

BACKGROUND OF THE INVENTION

Various types of electrosurgical devices are known and used in the medical field. Typically, such devices include a conductive tip that serves as an electrode in an electrical circuit which is completed either via a return electrode coupled to the patient or a return electrode mounted on the same device. Cutting and coagulation are essential operations of many electrosurgical devices. While the waveform of the supplied power to the electrode may affect the result, to a large extent the effect produced by a given device is determined by the density of the Radio Frequency (RF) current passing from the active electrode of the device to the tissue at the surgical site. High current density causes arcing to the tissue so as to produce cutting or bulk vaporization. Low current density causes tissue desiccation and hemostasis.

Bleeding is a common, yet undesired occurrence in medical surgical procedures because they may pose a threat to the patient, obscure the field of vision of the surgeon and interfere with the medical procedure. Stopping bleeding is time consuming and may be irritating to the physician. Various approaches to treat bleeding during surgery including medications, dressing and specialty devices are known Another approach used in electrosurgical devices to switch from a cutting/evaporation mode to a coagulation mode is to change the power to the electrosurgical device, change the waveform, or both. For example, the medical staff may use a special interrupted waveform, like COAG, and a lower power level in order to treat bleeding. The problem with prior art electrosurgical devices has been that it is difficult to achieve both cutting/evaporation and coagulation in the same instrument even if a COAG waveform and a reduced power level are used either independently or jointly.

Muller et al. in U.S. Pat. No. 7,364,579 teaches an electrocautery device for achieving hemostasis, the device having an electrically conductive element, the element being either a freely rotating spherical element, or a "plug made of an electrically conductive porous material". Also that "the conductive fluid emanating from the electrode/tip conducts the RF electrocautery energy away from the distal tip so that it is primarily the fluid, rather than the distal tip that actually accomplishes the cauterizing of tissue." The devices taught by Mulier have geometry configured for cautery of surfaces and are used in conjunction with other cutting devices. The devices themselves are incapable of cutting tissue. In U.S. Pat. No. 7,794,460 Mulier et al. teaches a "fluid delivered out of a hollow electrocautery electrode/tip creates a virtual electrode which incises and cauterizes the tissue." Although it is claimed that the fluid may "incise" the tissue, because the applied fluid spreads out freely over the tissue, it is incapable of "incising" or cutting the tissue. The device taught by Mulier is a cauterizing device only, both because of its electrode configuration (no cutting edges) and its continuous irrigant flow In view of the foregoing problems it has been recognized as desirable to find an improved surgical device effective both for cutting/evaporation and also coagulation without the need to change either the power or the waveform.

SUMMARY OF THE INVENTION

In view of the foregoing considerations, the present invention is directed to an improved, dual-mode instrument. The present invention discloses devices having the ability to quickly change the current density at the electrode during use and thereby switch from the cutting/evaporation mode to the coagulation mode (dual-mode). In a first embodiment the current density is reduced by supplying an irrigant on command to the site only when desiccation is desired, the conductivity of the irrigant stream causing current to be dispersed where irrigant is in contact with the tissue. In a second embodiment the electrode device has a cutting edge with two adjacent regions, a first configured for high current density cutting and bulk vaporization, and a second configured for low current density for desiccation, again with irrigation supplied to the site selectively so as to control the current density. In a third embodiment the active electrode is an assembly having a first movable element and a second fixed element, the movable element in a first position contacting the tissue as a cutting element, and with the movable element in a second position the second fixed element contacting tissue so as to produce desiccation. In yet a fourth embodiment a "brush" of non-conductive fibers (bristles) spreads conductive irrigant over the site so as to reduce the current density and produce desiccation. In a fifth embodiment the nonconductive fibers are randomly oriented so as to form a wool or mat which is saturated with conductive irrigant which forms a conductive path for RF energy to tissue which contacts the nonconductive wool.

Irrigant may be supplied to the device by gravity from a hung bag, by a manual pump activated by the surgeon, or by a mechanical pump. Irrigant may be supplied to the surgical site upon manual action, or electrical activation by the surgeon.

Devices formed in accordance with the principles of this invention may be used for any surgical procedure in which highly vascular tissue is cut electrosurgically in a dry or semi-dry field. Examples include but are not limited to tonsillectomy, liver resection, and cosmetic procedures such as breast augmentation, breast reduction or tummy tucks.

The above-noted objects and features of the invention will become more fully apparent when the following detailed description is read in conjunction with the accompanying figures and/or examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, it will be understood by those skilled in the art that one or more aspects of this invention can meet certain of the above objectives, while one or more other aspects can meet certain other objectives. Each objective may not apply equally, in all its respects, to every aspect of this invention. As such, the objectives disclosed herein should be viewed in the alternative with respect to any one aspect of this invention.

BRIEF DESCRIPTION OF THE FIGURES

Various aspects and applications of the present invention will become apparent to the skilled artisan upon consideration of the brief description of the figures and the detailed description of the present invention and its preferred embodiments that follows:

FIG. 14 is a plan view of an electrode for use in another alternate embodiment.

FIG. 15 is a side elevational view of the objects of FIG. 14.

DESCRIPTION OF THE PREFERRED EMBODIMENTS

Figure 1:
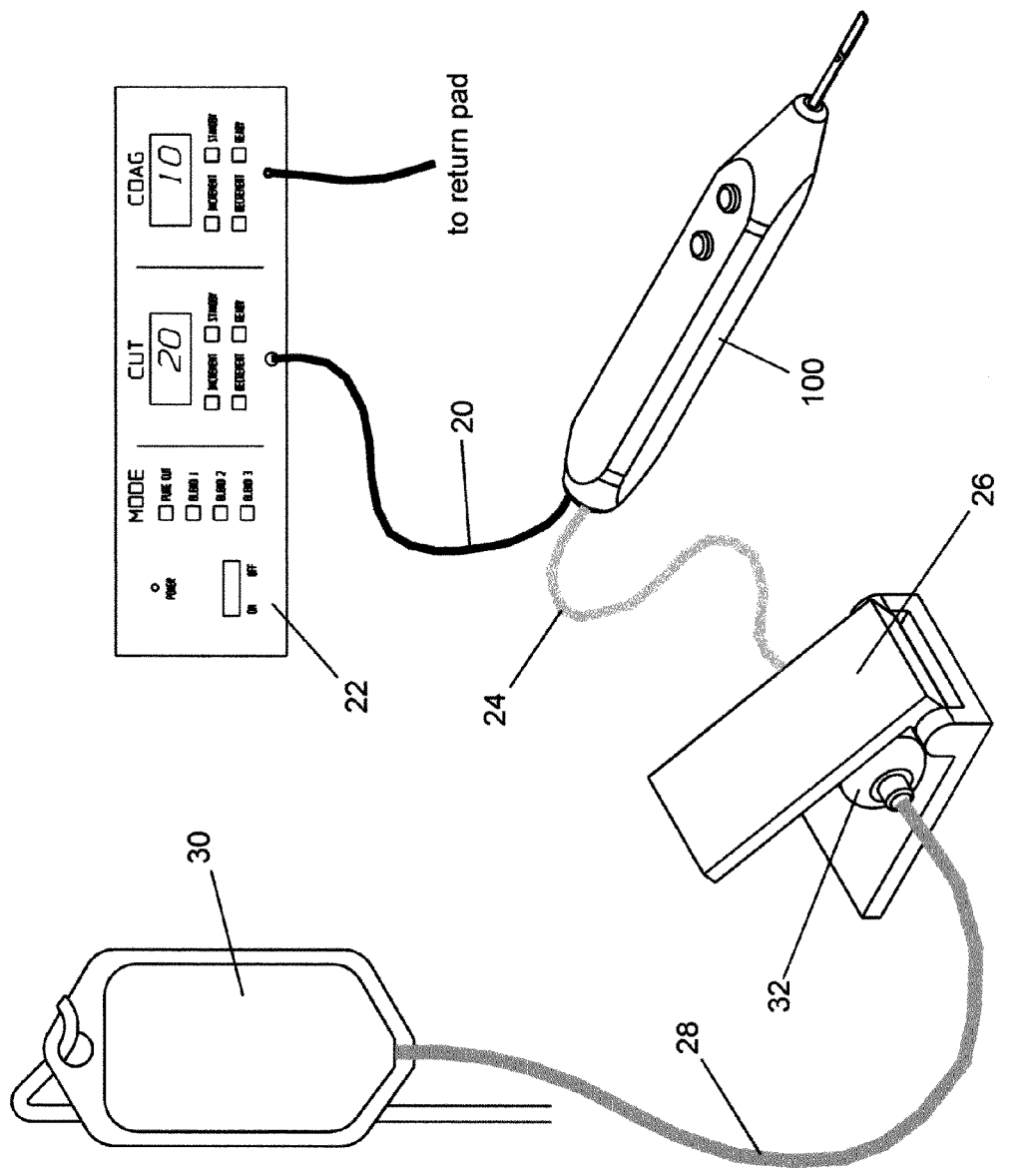
FIG. 1 depicts and electrosurgical system constructed in accordance with the principles of this invention.
Figure 2:
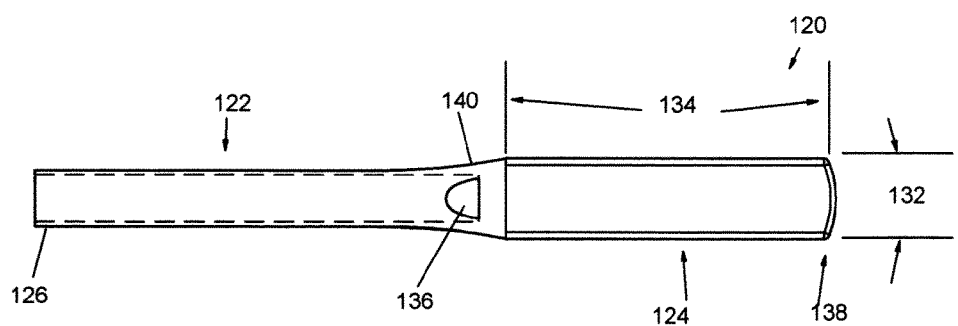
FIG. 2 is a plan view of an active electrode for an electrosurgical device and system constructed in accordance with the principles of this invention.
Figure 3:
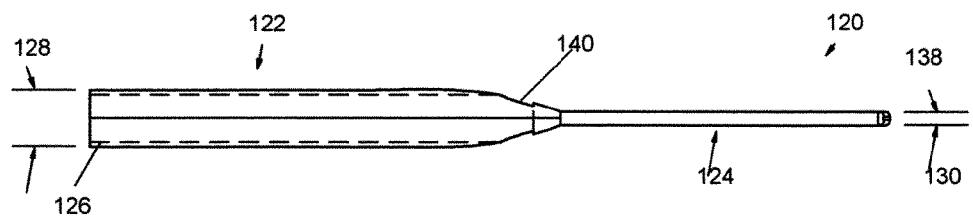
FIG. 3 is a side elevational view of the objects of FIG. 2.
Figure 4:
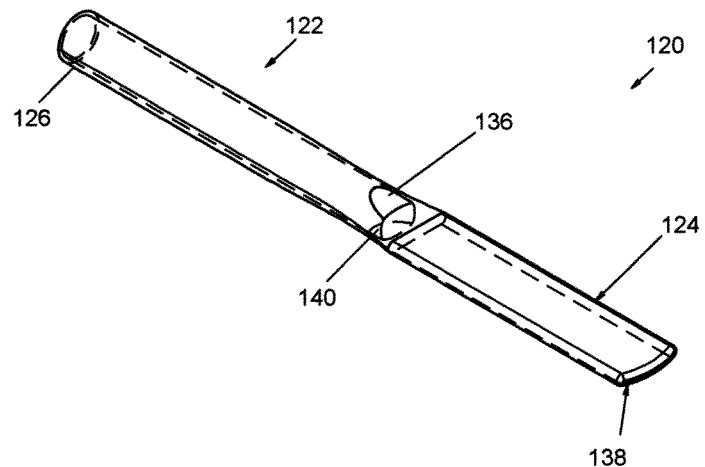
FIG. 4 is a perspective view of the objects of FIG. 2.
Figure 5:
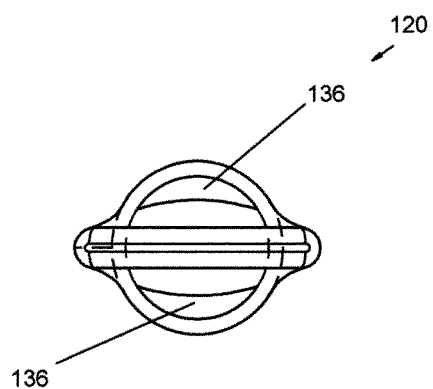
FIG. 5 is a distal axial view of the objects of FIG. 2.
Figure 6:
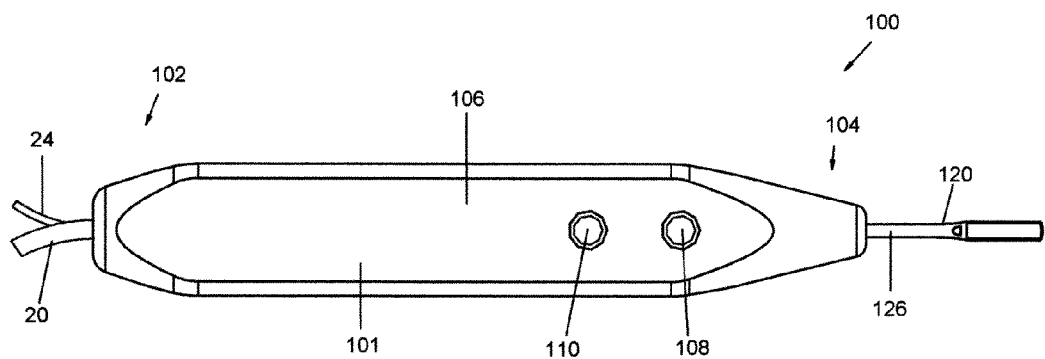
FIG. 6 is a plan view of an electrosurgical device for use with the active electrode of FIG. 2.
Figure 7:
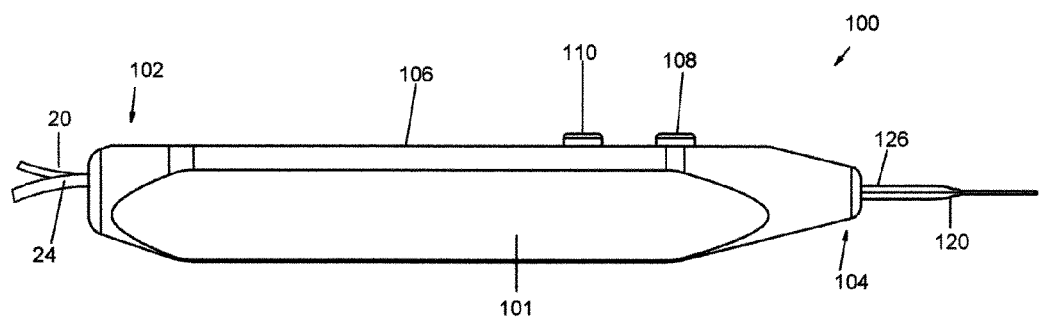
FIG. 7 is a side elevational view of the objects of FIG. 6.
Figure 8:
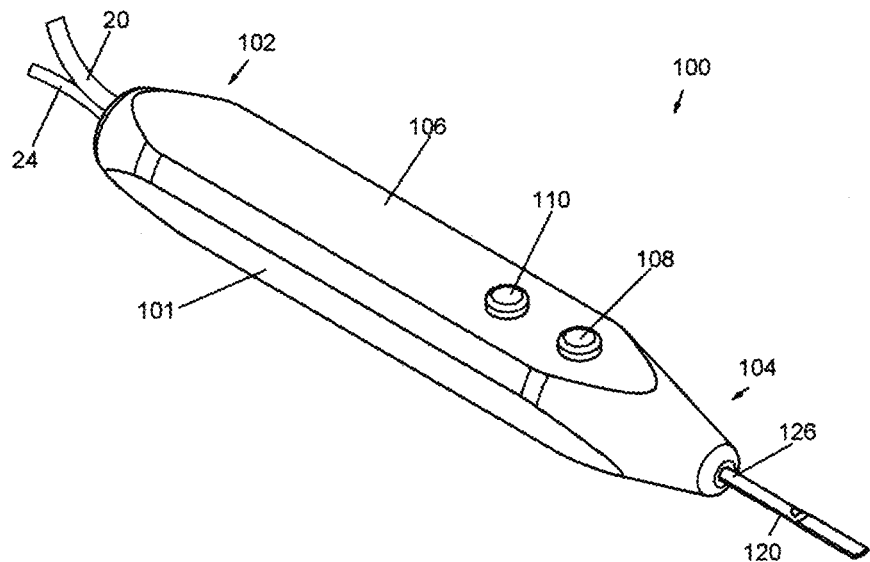
FIG. 8 perspective views of the objects of FIG. 6.
Figure 9:
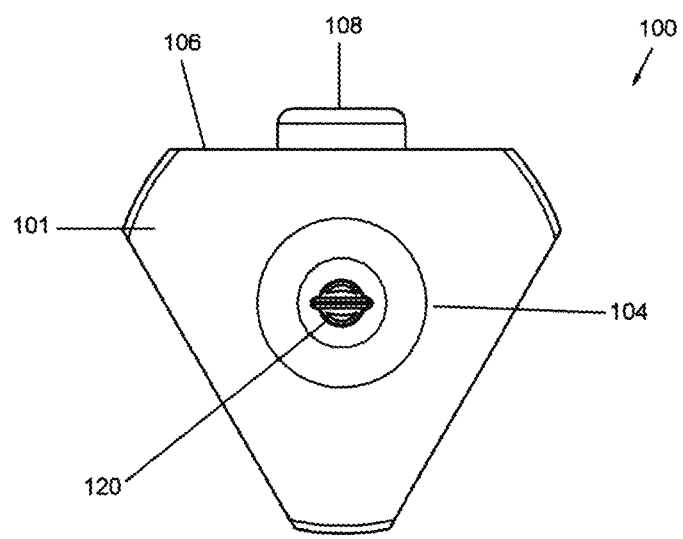
FIG. 9 is a distal axial view of the objects of FIG. 6.
Figure 10:
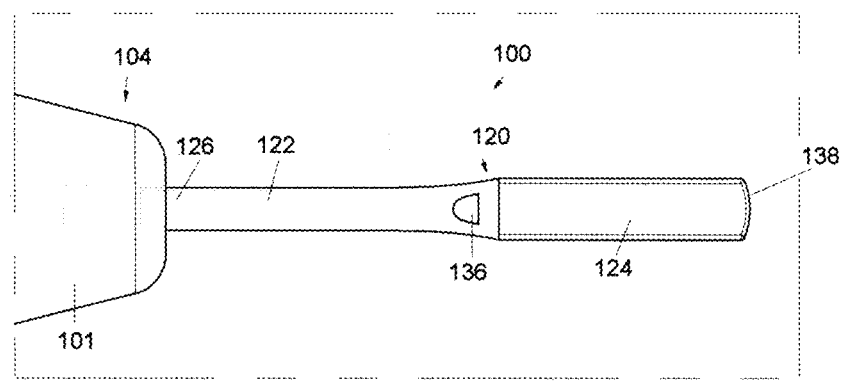
FIG. 10 is an expanded view of the distal portion of FIG. 6.
Figure 11:
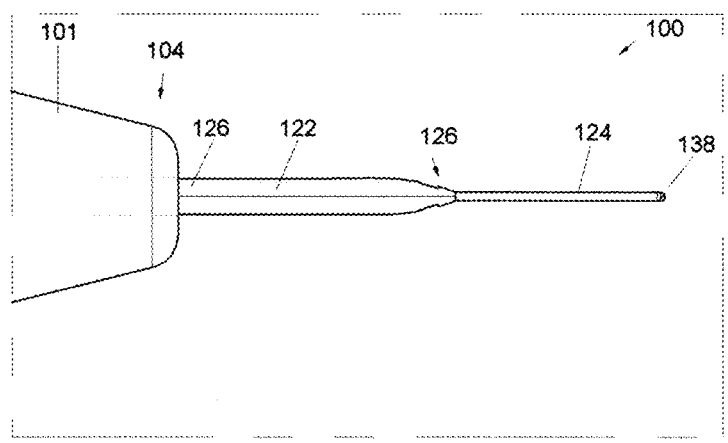
FIG. 11 is a side elevational view of the objects of FIG. 10.
Figure 12:
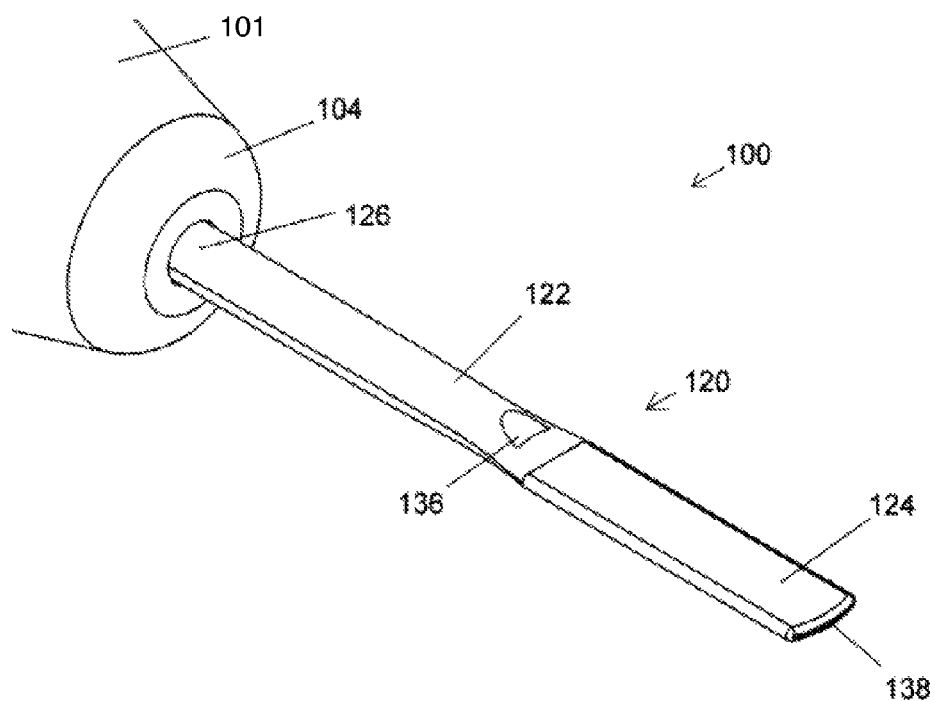
FIG. 12 is a perspective view of the objects of FIG. 10.
Figure 13:
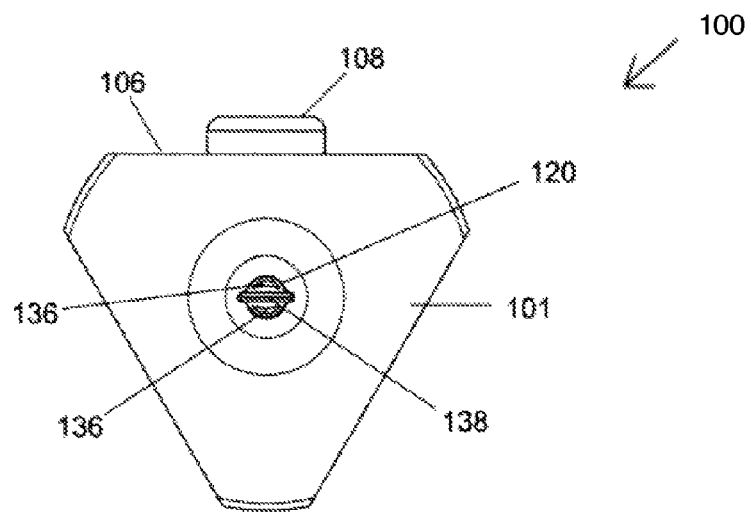
FIG. 13 is a distal axial view of the objects of FIG. 10.
Figure 16:
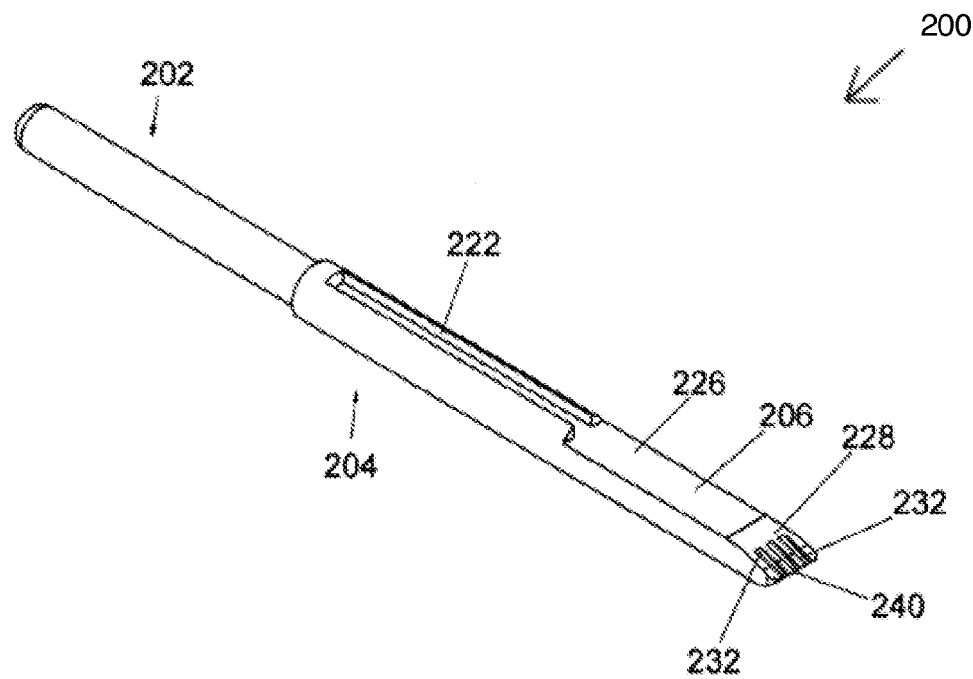
FIG. 16 is a perspective view of the objects of FIG. 14.
Figure 17:
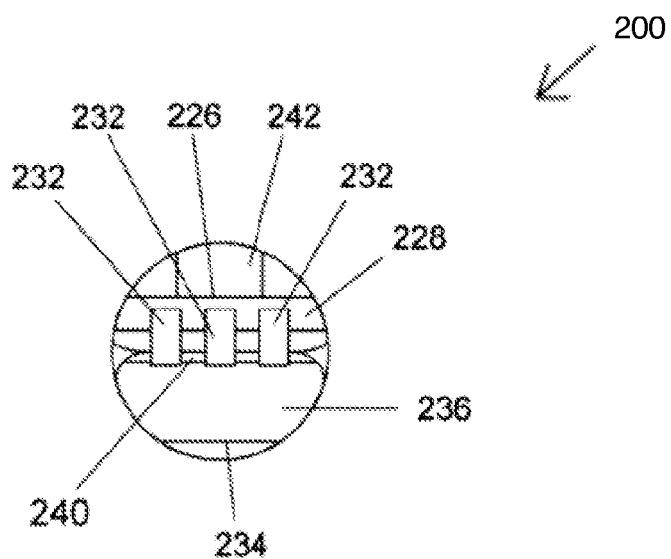
FIG. 17 is a distal axial view of the objects of FIG. 14.
Figure 18:
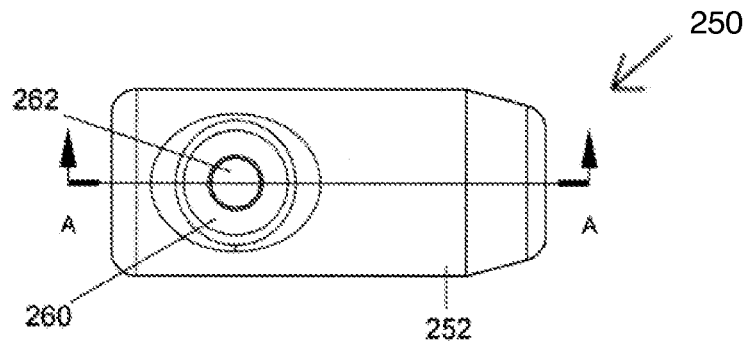
FIG. 18 is a plan view of an irrigation collar for use with the electrode of FIG. 14.
Figure 19:
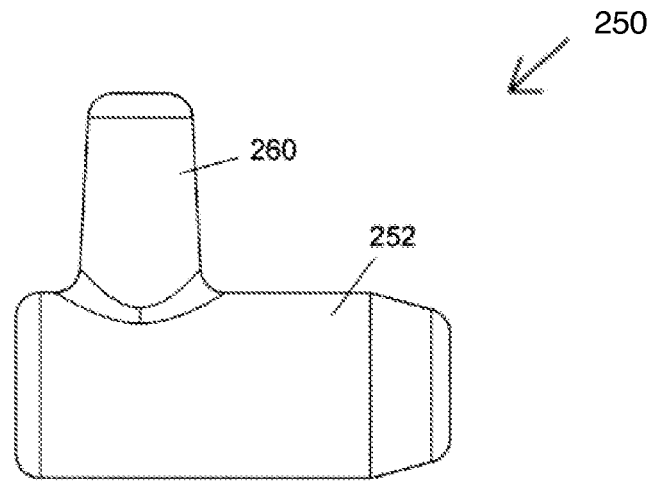
FIG. 19 is a side elevational view of the objects of FIG. 18.
Figure 20:
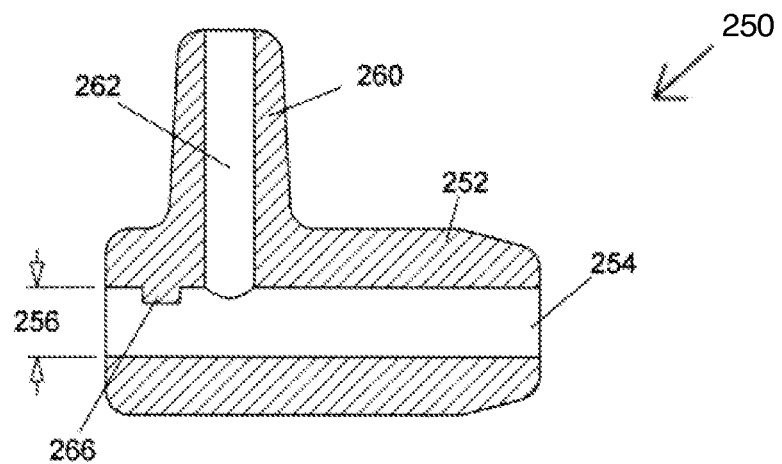
FIG. 20 is a side elevational sectional view of the objects of FIG. 14 at location A-A of FIG. 18.
Figure 21:
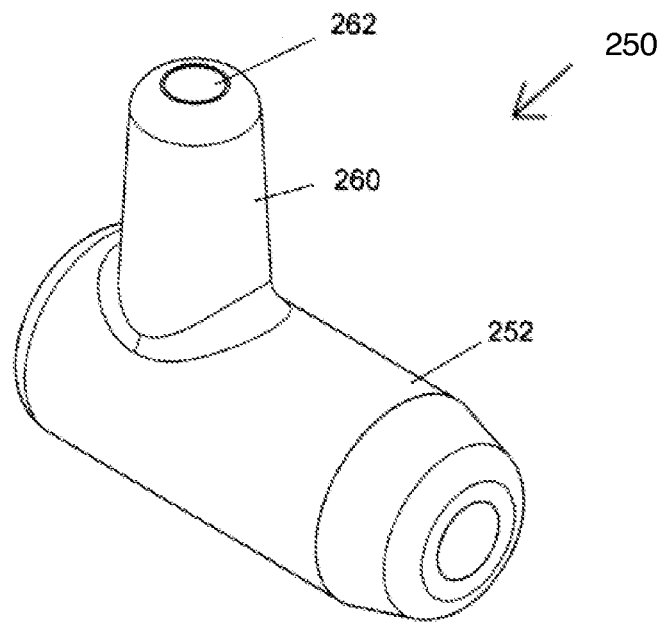
FIG. 21 is a perspective view of the objects of FIG. 18.
Figure 22:
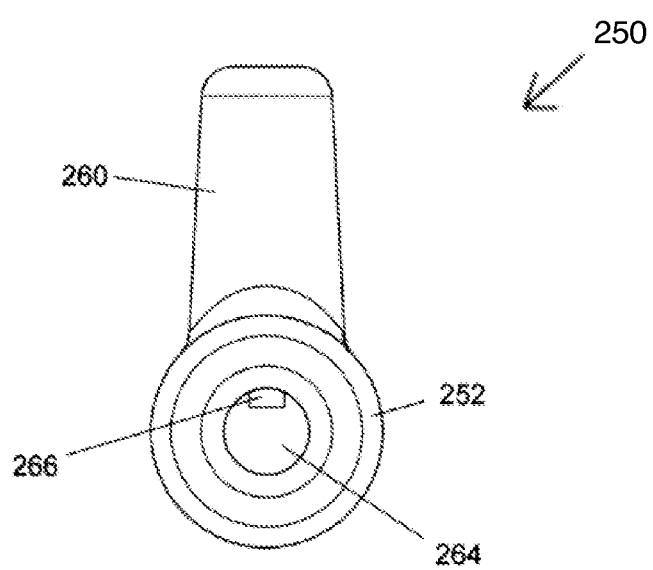
FIG. 22 is a distal axial view of the objects of FIG. 18.
Figure 23:
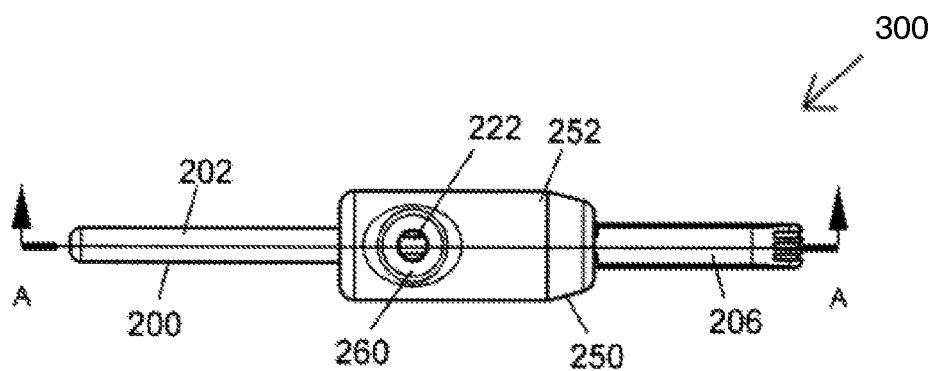
FIG. 23 is a plan view of the electrode of FIG. 14 assembled to the irrigation collar of FIG. 18.
Figure 24:
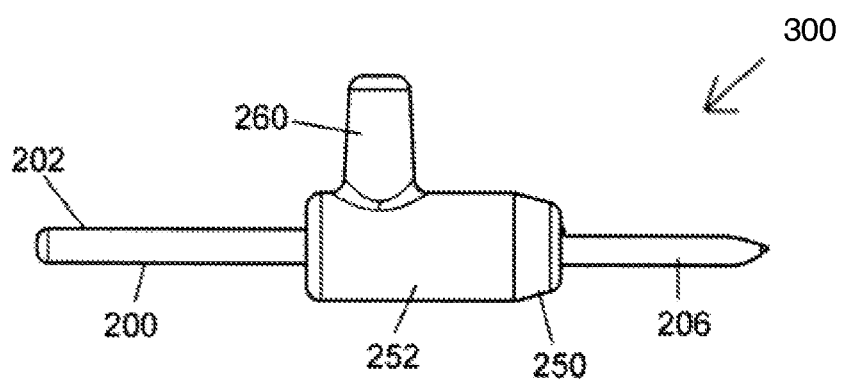
FIG. 24 is a side elevational view of the objects of FIG. 23.
Figure 25:
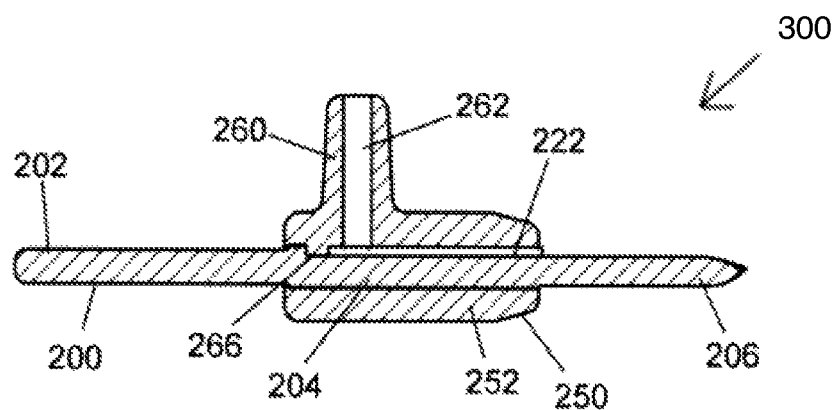
FIG. 25 is a side elevational sectional view of the objects of FIG. 23 at location A-A of FIG. 23.
Figure 26:
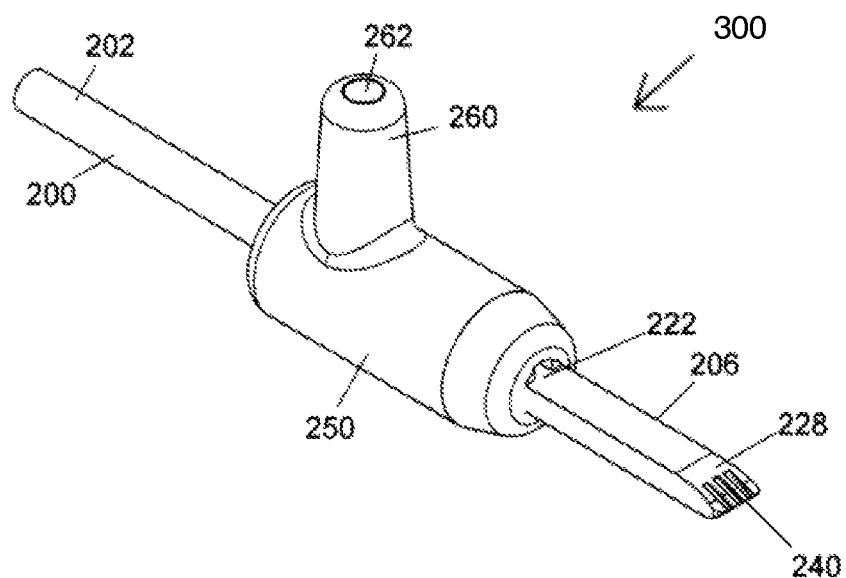
FIG. 26 is a perspective view of the objects of FIG. 23.
Figure 27:
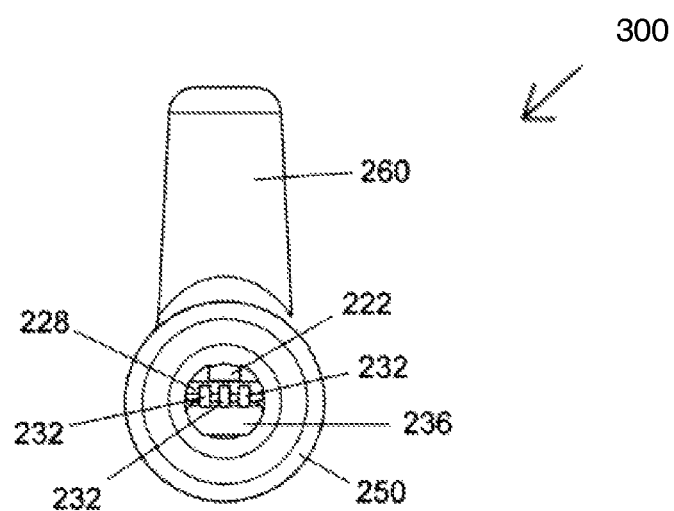
FIG. 27 is a distal axial view of the objects of FIG. 23.
Figure 28:
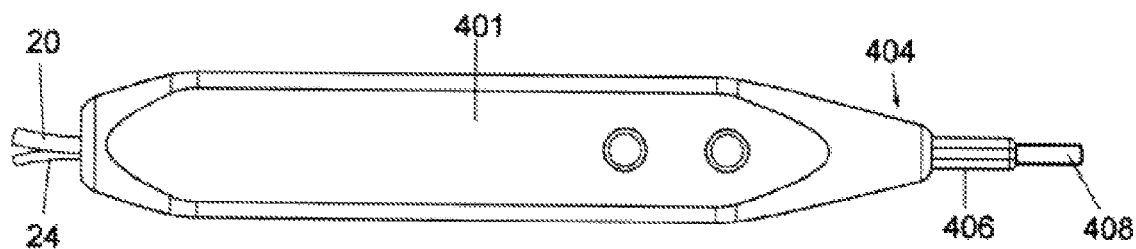
FIG. 28 is a plan view of another alternate embodiment having an extendable active electrode element and constructed in accordance with the principles of this invention, the active electrode being in a first extended position.
Figure 29:
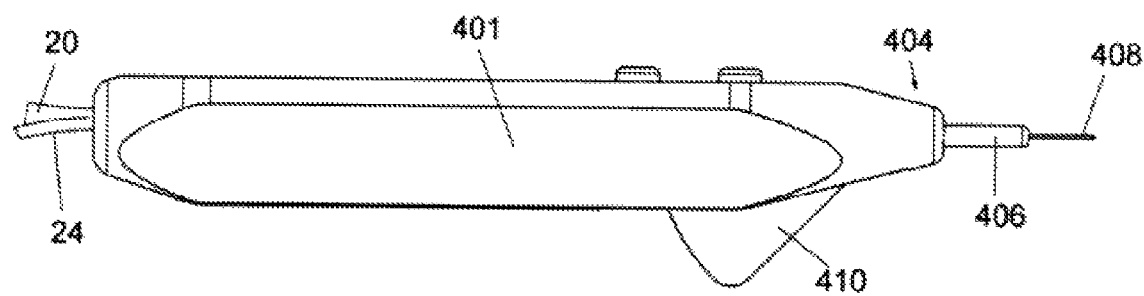
FIG. 29 is a side elevational view of the objects of FIG. 28.
Figure 30:
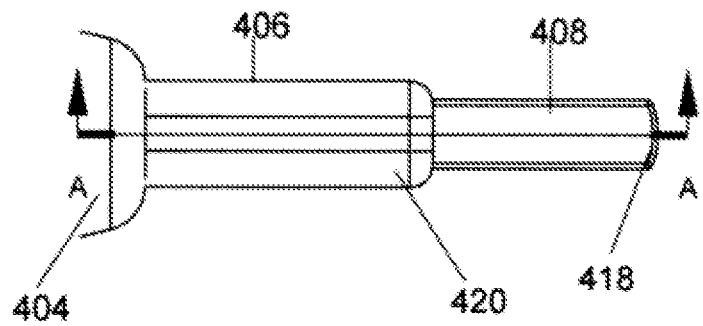
FIG. 30 is a plan view of the distal portion of the objects of FIG. 28.
Figure 31:
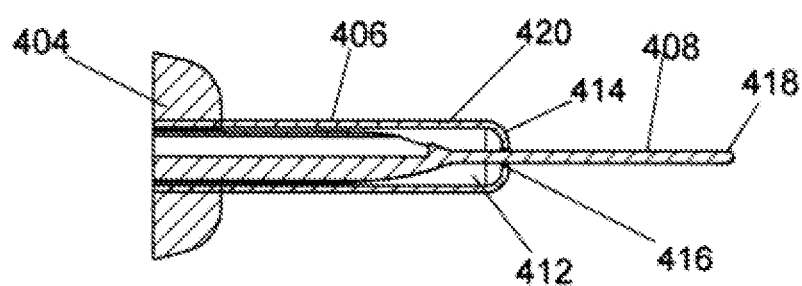
FIG. 31 is a side elevational sectional view of the objects of FIG. 30 at location A-A of FIG. 30.
Figure 32:
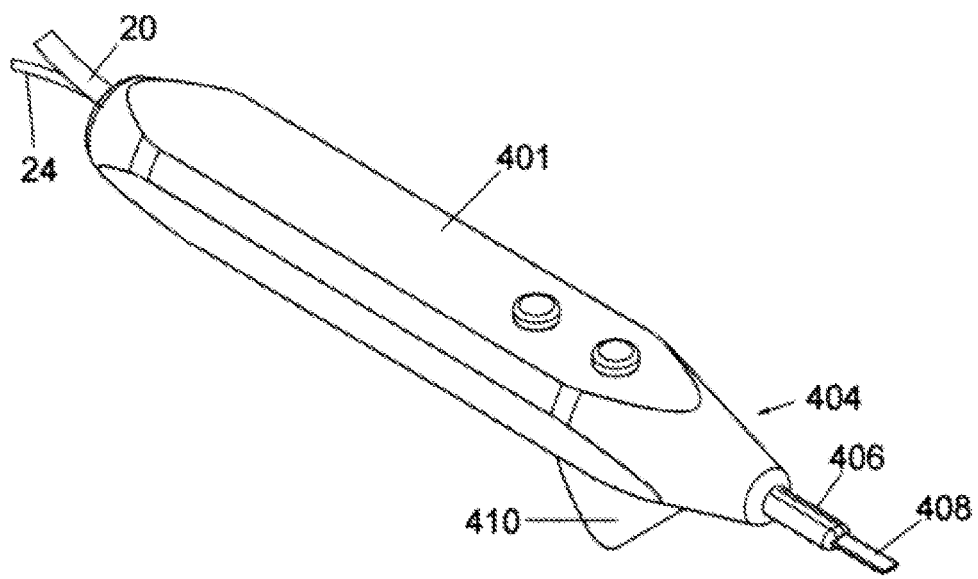
FIG. 32 is a perspective view of the objects of FIG. 28.
Figure 33:
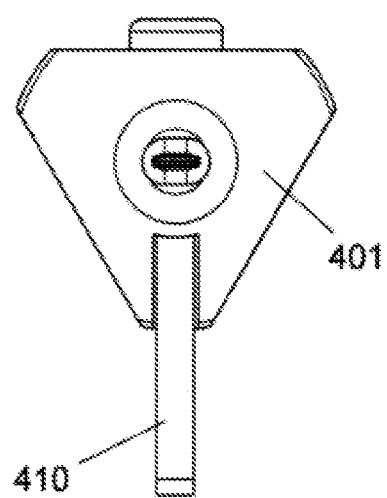
FIG. 33 is a distal axial view of the objects of FIG. 28.
Figure 34:
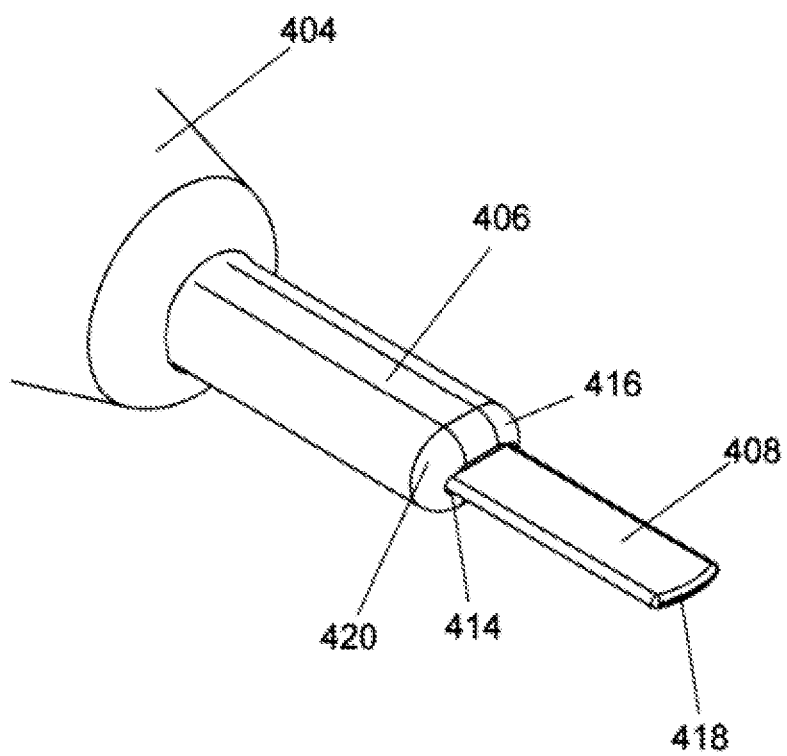
FIG. 34 is an expanded perspective view of the distal portion of the objects of FIG. 32.
Figure 35:
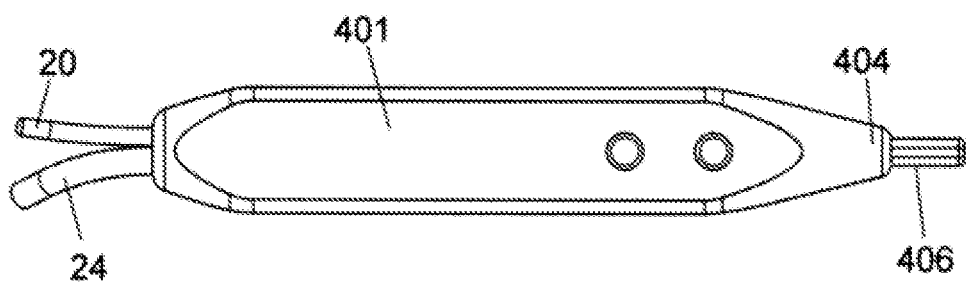
FIG. 35 is a plan view of the alternate embodiment of FIG. 28 with the extendable active electrode element in the second retracted position.
Figure 36:
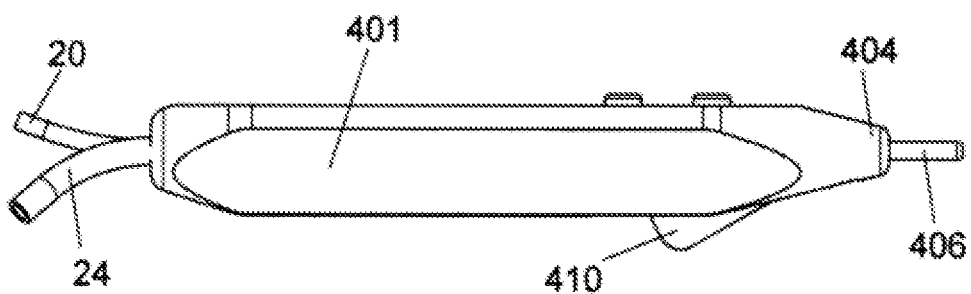
FIG. 36 is a side elevational view of the objects of FIG. 35.
Figure 37:
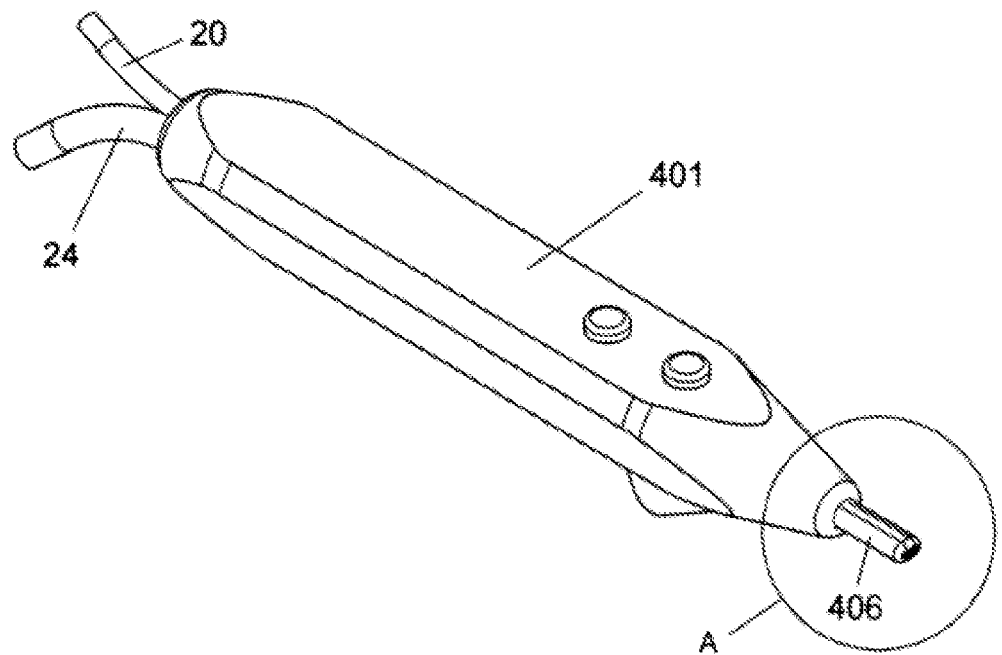
FIG. 37 is a perspective view of the objects of FIG. 35.
Figure 38:
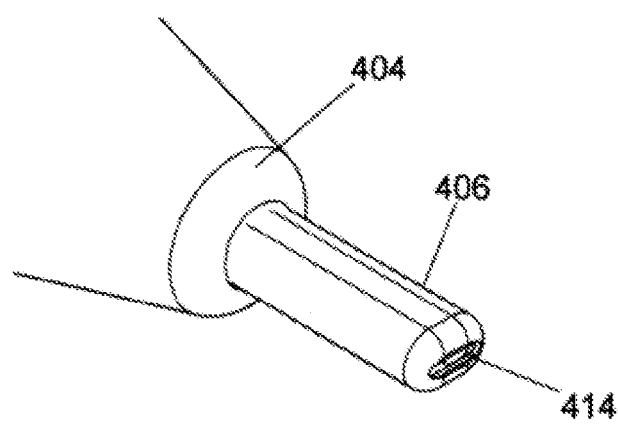
FIG. 38 is an expanded perspective view of the distal portion of the objects of FIG. 37.
Figure 39:
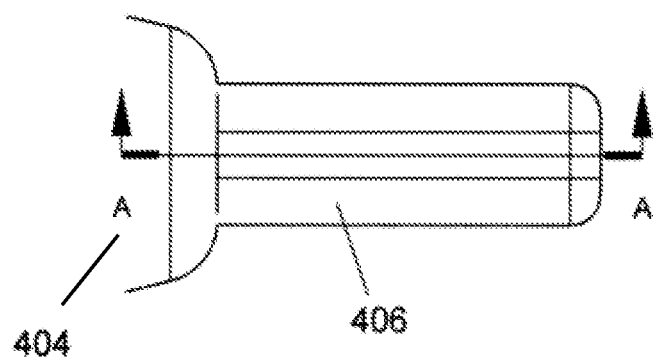
FIG. 39 is an expanded plan view of the objects of FIG. 37.

A unifying concept of the embodiments of this invention is the ability of the devices herein disclosed to function in a first mode in which high-density RF energy is used to cut or vaporize tissue, and a second mode in which lower-density RF energy desiccates tissue to produce hemostasis. Although any methods and materials similar or equivalent to those described herein can be used in the practice or testing of embodiments of the present invention, the preferred methods, devices, and materials are now described. However, before the present materials and methods are described, it is to be understood that this invention is not limited to the particular compositions, methodologies or protocols herein described, as these may vary in accordance with routine experimentation and optimization. It is also to be understood that the terminology used in the description is for the purpose of describing the particular versions or embodiments only, and is not intended to limit the scope of the present invention which will be limited only by the appended claims.

DEFINITIONS

In the context of the present invention, the following definitions apply:

The words "a", "an", and "the" as used herein mean "at least one" unless otherwise specifically indicated.

In common terminology and as used herein, the term "electrode" may refer to one or more components of an electrosurgical device (such as an active electrode or a return electrode) or to the entire device, as in an "ablator electrode" or "cutting electrode". Such electrosurgical devices are often interchangeably referred to herein as electrosurgical "probes" or "instruments".

The present invention makes reference to an "active electrode" or "active element". As used herein, the term "active electrode" refers to one or more conductive elements formed from any suitable metallic material, such as stainless steel, nickel, titanium, tungsten, and the like, connected, for example via cabling disposed within the elongated proximal portion of the instrument, to a power supply, for example, an externally disposed electrosurgical generator, and capable of generating an electric field.

In certain embodiments, the present invention makes reference to a "return electrode". As used herein, the term "return electrode" refers to one or more powered conductive elements to which current flows after passing from the active electrode(s) back to the electrical RF generator. This return electrode may be located on the ablator device or in close proximity thereto and may be formed from any suitable electrically conductive material, for example a metallic material such as stainless steel, nickel, titanium, tungsten, aluminum and the like. Alternatively, one or more return electrodes, referred to in the art as "dispersive pads" or "return pads", may be positioned at a remote site on the patient's body.

In certain embodiments, the present invention makes reference to "fluid(s)". As used herein, the term "fluid(s)" refers to liquid(s), either electrically conductive or non-conductive, and to gaseous material, or a combination of liquid(s) and gas(as).

The term "proximal" refers to that end or portion which is situated closest to the user; in other words, the proximal end of an electrosurgical instrument of the instant invention will typically include the handle portion.

The term "distal" refers to that end or portion situated farthest away from the user; in other words, the distal end of an electrosurgical instrument of the instant invention will typically include the active electrode portion.

In certain embodiments, present invention makes reference to the vaporization of tissue. As used herein, the term "tissue" refers to biological tissues, generally defined as a collection of interconnected cells that perform a similar function within an organism. Four basic types of tissue are found in the bodies of all animals, including the human body and lower multicellular organisms such as insects, including epithelium, connective tissue, muscle tissue, and nervous tissue. These tissues make up all the organs, structures and other body contents. The present invention is not limited in terms of the tissue to be treated but rather has broad application to the vaporization any target tissue with particular applicability to the ablation, destruction and removal of problematic joint tissues.

The instant invention has both human medical and veterinary applications. Accordingly, the terms "subject" and "patient" are used interchangeably herein to refer to the person or animal being treated or examined. Exemplary animals include house pets, farm animals, and zoo animals. In a preferred embodiment, the subject is a mammal.

Unless otherwise defined, all technical and scientific terms used herein have the same meaning as commonly understood by one of ordinary skill in the art to which this invention belongs. In case of conflict, the present specification, including definitions, will control.

EXAMPLES

Hereinafter, the present invention is described in more detail by reference to the exemplary embodiments. However, the following examples only illustrate aspects of the invention and in no way are intended to limit the scope of the present invention. As such, embodiments similar or equivalent to those described herein can be used in the practice or testing of the present invention.

FIG. 1 depicts an electrosurgical system constructed in accordance with the principles of this invention. Electrosurgical device 100 constructed in accordance with the principles of this invention is connected by cord 20 to electrosurgical generator 22, and by tubular element 24 to flow control element 26, and therethrough by tubular member 28 to irrigant source 30. In the preferred embodiment depicted, control element 26 is a foot control; in others control element 26 is a valve controlled by electrosurgical device 100. The foot control 26 depicted has a fluid control means 32 which may be a valve which allows irrigant from source 30 to flow to device 100 when the foot control 26 is depressed. In another embodiment, foot control 26 fluid control means 32 is a deformable vessel having valves such that depressing the foot pedal causes a volume of irrigant to be expelled from the vessel and supplied to device 100 via tube 20. When the volume is expelled, the foot pedal is allowed to return to its first position and the vessel refills with irrigant from source 30 via tube 28.

It will be understood that foot control 26 may be replaced with another control means without departing from the principles of this invention. For instance, the control means may be part of the handle with an activation means such as a button or deformable vessel, or may be combined with the button for activating the electrosurgical generator such that activating the generator in a coagulate mode causes saline to flow to the surgical site.

In one embodiment tubular element 28, fluid control means 32 and tubular member 24 are a tubing set having at the proximal end of element 28 a conventional spike for connection to an irrigant bag, and having at the distal end of element 24 a connector for attachment to device 100. In another embodiment the tubing set is attached to and packaged with device 100. In other embodiments elements are 24, 28 and 32 are discrete elements.

FIGS. 2 through 5 depict an active electrode 120 constructed in accordance with the principles of this invention. Electrode 120 is formed from a suitable metal tubing of diameter 128, the distal portion 124 of length 134 being coined to a thickness 130 and width 132 and the proximal portion 122 retaining its original shape. Distal-most end 138 may be trimmed to a predetermined desired shape such as, for instance, flat, arcuate, or having serrations or other irregularities to enhance cutting performance. Irrigation ports 136 at distal end 140 of proximal portion 122 are in communication with the lumen of proximal portion 122. In a preferred embodiment, there are ports on the top and bottom side of electrode 120. In other embodiments there is a port on the top only or on the bottom only.

As seen in FIGS. 6 through 13, handle 101 of electrosurgical device 100 has a proximal end 102 from which pass cable 20 and tubular member 24, and a distal end 104 to which is mounted proximal end 126 of electrode 120. Means within handle 101 allow communication between the lumen of proximal portion 122 of electrode 120 and tubular member 24 such that irrigant from source 30 flows to irrigation ports 136 and therethrough to the surgical site when flow control 26 is activated. Handle 101 has a top surface 106 positioned on which are first button 108 and second button 110, buttons 108 and 110 providing means for controlling electrosurgical generator 22 such that when button 108 is depressed RF current of a first waveform and first power level are supplied via means within device 100 to electrode 120. When second button 110 is depressed, RF current of a second waveform and second power level are supplied to electrode 120.

In use distal portion of 124 of electrode 120 is used to cut tissue. Irrigant is not supplied to the site, any fluid present being blood or other body fluids. Because the site is relatively dry, RF energy flows only from portions of portion 124 which contact or are in close proximity to tissue. If bleeding is encountered, footpedal 26 is depressed causing irrigant from supply 30 to flow to the surgical site. With conductive irrigant present, current flows from all portions of the electrode which are in contact with the irrigant to all portions of the tissue which are in contact with the irrigant. Because the area of tissue to which current flows is much greater than when operating in a dry environment without conductive irrigant, the energy density is much lower. The low density RF energy desiccates tissue in contact with the saline puddle so as to stop bleeding. When hemostasis has been achieved, the saline flow is terminated. When irrigant has been drained or removed from the region, cutting resumes.

The flat sides of distal portion 124 of electrode 120 may be used to desiccate tissue in the presence of conductive irrigant. For instance, with the device activated, the surgeon may activate the irrigant flow intermittently while "painting" the surface of tissue with a portion of a side of distal portion 124 of electrode 120 thereby desiccating tissue at the surface prior to cutting with electrode 120. During this desiccation prior to cutting, the current density is reduced by the presence of the conductive irrigant which wets the region in proximity to distal portion 124 of electrode 120. When the edge or distal tip of portion 124 of electrode 120 is subsequently applied to the tissue without supplied irrigant, the resulting cutting of the tissue has decreased instances of bleeding due to the prior desiccation of the region. Indeed, when bleeding is encountered during cutting, painting of the tissue surface in proximity to the bleeder with a planar surface of distal portion 124 of electrode 120 in the presence of supplied conductive irrigant causes desiccation of the region and hemostasis. Thereafter cutting can be resumed when collected irrigant has drained from the region.

FIGS. 14 through 17 depict an electrode 200 for an alternate embodiment formed in accordance with the principles of this invention. Electrode 200 has a proximal portion 202 of diameter 210 and length 212 suitable for mounting in a standard electrosurgical pencil. Middle portion 204 of diameter 220 larger than diameter 210 and length 230 has formed therein axial channel 222 having a bottom surface 224 coplanar with first surface 226 of distal portion 206 and terminating at its proximal end in proximal surface 242. Distal to planar surface 226 first distal end surface 228 has formed therein grooves 232. Second distal surface 234 terminates in distal radius 236. Distal radius 236 of second surface 234 and first distal end surface 228 together form distal edge 240.

FIGS. 18 through 22 depict an irrigation collar 250 for use with electrode 200 and constructed in accordance with the principles of this invention. Collar 250 has a tubular axial portion 252 having a lumen 254 of diameter 256, diameter 256 of lumen 254 being slightly small than diameter 220 of middle portion 204 of electrode 200, and a tapered tubular lateral portion 260 having a lumen 262, lumens 262 and 254 being in communication. Lumen 254 has formed therein alignment key 266.

FIGS. 23 through 27 depict an alternate embodiment device constructed in accordance with the principles of this invention. Device 300 is constructed by inserting electrode 200 into irrigation collar 250, the angular alignment and relative axial position being established by channel 222 and key 266. Because lumen 254 is slightly smaller than diameter 220 of middle portion 204 of electrode 200, friction between the mating surfaces prevents unintended disassembly. Lumen 262 is in communication channel 222 such that when tubular member 24 (FIG. 1) is attached to tapered lateral portion 260 of irrigation collar 250 a path is established for irrigant such that when flow control 26 is activated, irrigant from source 30 is supplied to the surgical site via channel 222.

In use, proximal end 202 of electrode 200 is inserted into a standard electrosurgical pencil. Tapered lateral portion 260 of collar 200 is connected to tubular element 24 (FIG. 1), and therethrough to irrigant supply 30 with which it communicates. In a first mode of operation, irrigant is not supplied to the surgical site and any fluids present are blood or other body fluids. Current flows only from portions of the electrode in contact with, or in close proximity to tissue. Accordingly, the surgeon uses edge 240 to cut tissue and distal end surface 228 to vaporize regions of tissue, both regions being configured so as to produce high current densities. When bleeding occurs, irrigant from irrigant source 30 may be supplied to the site by activating footswitch 26 such that saline from tubular element 260 flows via lumen 262 to channel 222 and thereby to the distal end of distal region 206. The supplied saline diffuses the RF energy in the same manner as the previous embodiment. Alternatively, the energy may be diffused over a large by "painting" the bleeding tissue with distal radius 236 of second surface 234, the surface having no features to increase current density. If desired, irrigant may be supplied to the site as the surface is painted thereby increasing the area over which power is dissipated so as to achieve lower current density and improved tissue desiccation.

In yet another alternate embodiment constructed in accordance with the principles of this invention the device has two modes of operation based on the position of an active electrode having two elements, one fixed and one axially movable between a first position and a second position. In the first position the movable electrode element contacts tissue and functions as a cutting device. In the second position the movable electrode element is retracted within the fixed element of the electrode so as to create an irrigation port. Irrigant is supplied to the surgical site and the fixed portion of the electrode contacts tissue so as to desiccate tissue in contact with the fixed element or the supplied irrigant or both.

Referring now to FIGS. 28 through 34 depicting the device 400 with the movable element of the active electrode in its first extended position. Handle 401 is identical to handle 101 in all aspects except as noted. Handle 401 has a distal end 404 to which are mounted an active electrode assembly having a closed-distal-end tubular fixed element 406 with a distal end 420, inner lumen 412, and distal end wall 416 in which is formed opening 414, and a movable blade element 408 having a distal end 418. Handle 401 also has a lever 410 for controlling the position of movable active blade element 408, lever 410 having a first position (shown) in which blade element 408 is extended and a second position in which blade element 408 is refracted. Through means within handle 401, lumen 412 is in communication with tube 24 and therethrough with irrigant supply 30 such that lumen 412 if filled with irrigant. Because movable element 408 is positioned within opening 414, irrigant cannot flow distally from lumen 412 therethrough.

Figure 40:
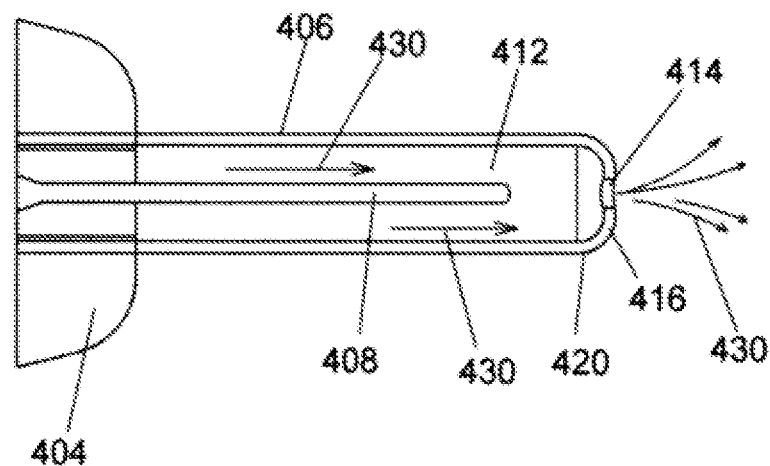
FIG. 40 is a side elevational sectional view of the objects of FIG. 39 at location A-A of FIG. 39.
Figure 41:
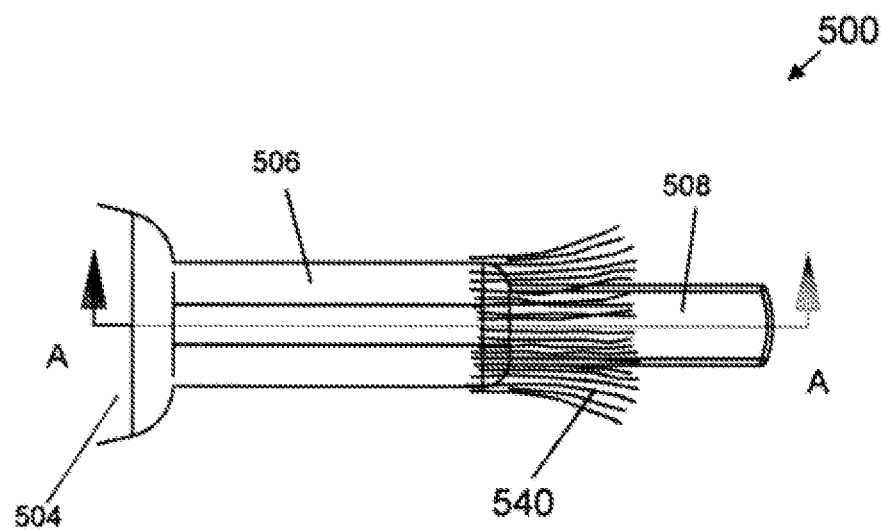
FIG. 41 is an expanded plan view of the distal portion of another alternate embodiment constructed in accordance with the principles of this invention, the embodiment being like the embodiment of FIGS. 28 through 40 but with nonconductive fibers affixed to the distal end of the fixed electrode element to form an electrode brush.
Figure 42:
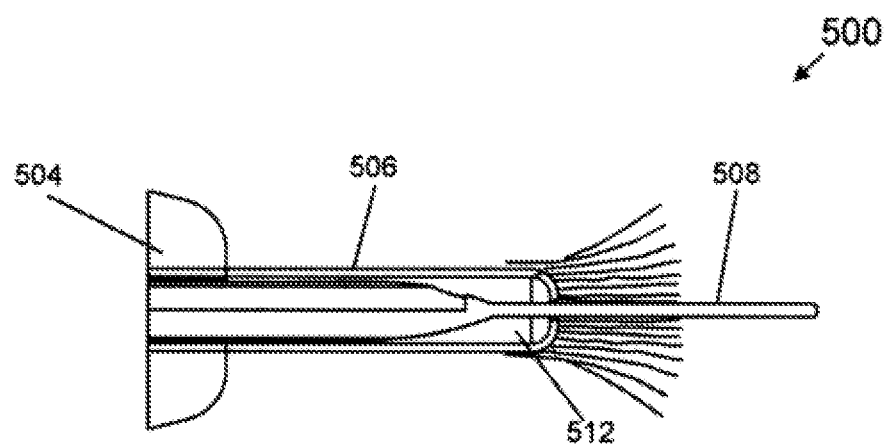
FIG. 42 is a side elevational sectional view of the objects of FIG. 41.
Figure 43:
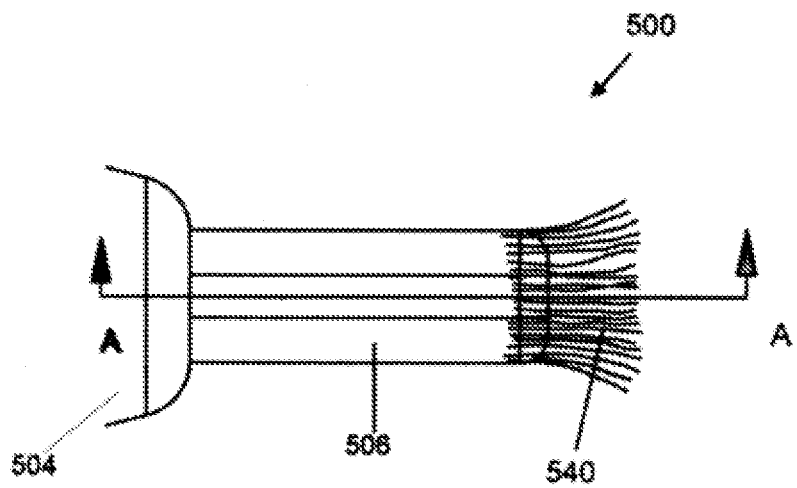
FIG. 43 is a plan view of the objects of FIG. 41 but with the movable electrode element being in the retracted position rather than the extended position of FIGS. 41 and 42.

FIGS. 35 through 40 depict device 400 with handle 410 in its second position and with the movable blade element 408 in the retracted position, distal end 418 being withdrawn into lumen 412 of fixed element 406 so as to allowing opening 414 in distal end wall 416 of fixed element 406 to function as an irrigation port. As best seen in FIG. 40, irrigant 430 flows through lumen 412 to opening 414 and therethrough to tissue in contact with or close proximity to distal end 420 of fixed element 406 so as to disperse RF energy of an area sufficient to cause desiccation of tissue.

Figure 44:
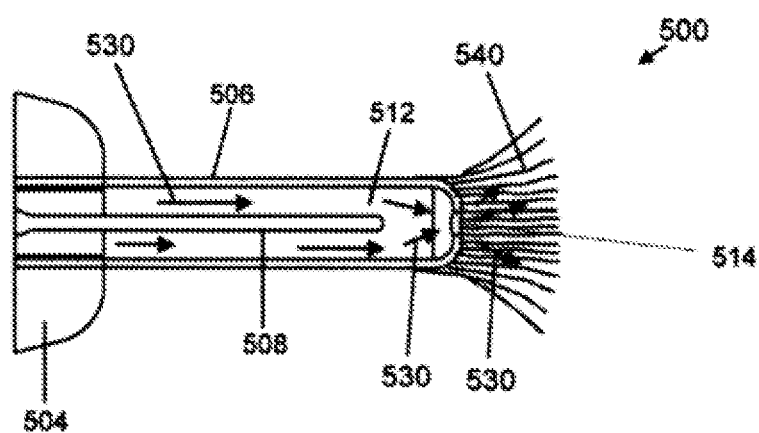
FIG. 44 is a side elevational sectional view of the objects of FIG. 43 at location A-A of FIG. 43.
Figure 45:
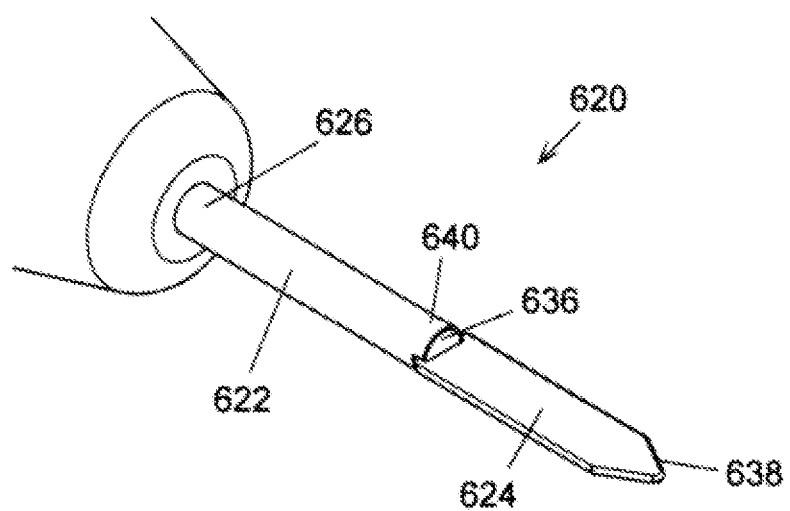
FIG. 45 is a perspective view of an alternate embodiment electrode of the instant invention.
Figure 46:
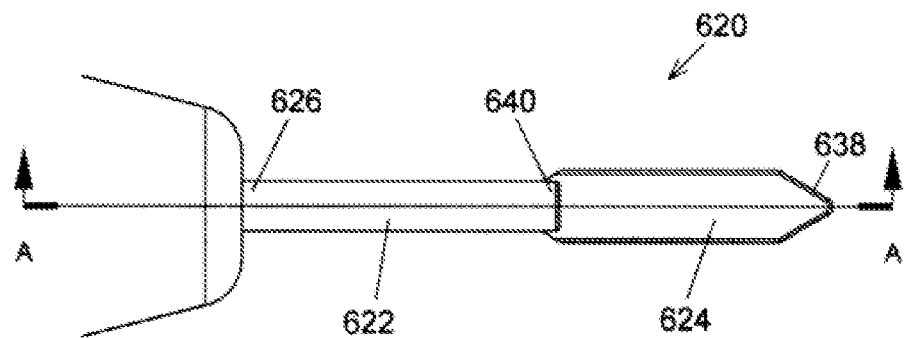
FIG. 46 is a plan view of the objects of FIG. 45.
Figure 47:
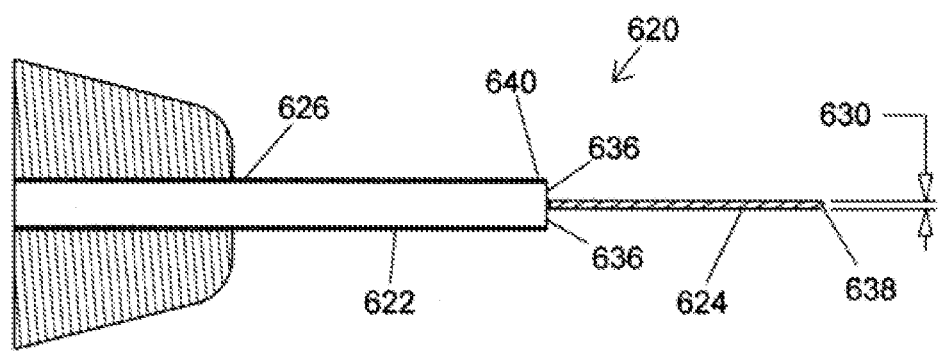
FIG. 47 is a side elevational sectional view of the objects of FIG. 46 at location A-A.
Figure 48:
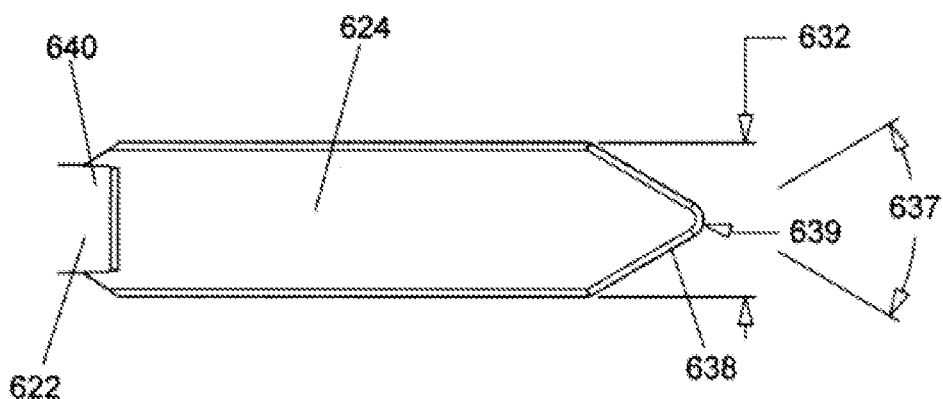
FIG. 48 is an expanded plan view of the distal portion of the objects of FIG. 46.

In yet another alternate embodiment of this invention, the dispersal of irrigant and therefore RF energy over an area is aided by nonconductive fibers (bristles) affixed to the distal end of the device so as to form a type of brush that provides pathways for the irrigant. In the illustrative depiction of such a device 500 shown in FIGS. 41 through 44, the handle is identical to handle 401 of the embodiment of FIGS. 28 through 40. Referring to FIGS. 41 through 44, movable active electrode element 508 is identical to element 408 of embodiment 400. Fixed electrode element 506 is like element 406 in that it has a distal end 520, inner lumen 512, and distal end wall 516 in which is formed opening 514. Additionally, nonconductive fibers 540 are affixed to distal end 520 of fixed element 506 surrounding opening 514 in distal end wall 516. As depicted in FIG. 44, in which movable blade element 508 in the retracted position, distal end 518 being withdrawn into lumen 512 of fixed element 506 so as to allowing opening 514 in distal end wall 516 of fixed element 506 to function as an irrigation port. Irrigant 530 flows through lumen 512 to opening 514 and therethrough to nonconductive fibers 540, fibers 540 directing and dispersing irrigant 530 to a region approximating the region of contact between the fibers and adjacent tissue. RF energy flowing through the irrigant is dispersed over the area defined by this region so as to decrease the current density to a level, which causes desiccation of tissue with resulting hemostasis.

In embodiment 500 the fibers are aligned like the bristles of a brush. In other embodiments the nonconductive fibers are randomly oriented to for a non-conductive wool, a mass of which is affixed to the fixed element of the active electrode. In these embodiments the conductive irrigant saturates the fibers such that any portion of the mass that contacts tissue will conduct low-density RF energy to the tissue so as to achieve hemostasis.

While embodiments with nonconductive fibers for enhancing and controlling the irrigant dispersal are depicted as modifications to device with movable active electrode elements, it will be recognized that other configurations using such fibers are possible and limited only by the desired medical application and the operational and engineering objectives of the designer.

FIGS. 45 through 48 depict an alternate embodiment electrode 620 of the present invention. Electrode 620 is configured like electrode 120 (FIGS. 10 through 13) in that is has a tubular proximal portion 622 and a planar distal portion 624. However, unlike electrode 120, which preferably has a unitary construction, electrode 620 is an assembly formed by irremovably affixing the proximal end of planar portion 624 to distal end of the tubular portion 622 by welding, brazing or mechanical assembly, wherein it is preferred that both elements are formed of a suitable metallic material. Distal planar portion 624 has a width 632 and thickness 630. Distal edge 638 has a wedge shape of included angle 637 when viewed in a plan view, having a distal-most radius 639 formed thereon. Distal end 640 of proximal tubular element forms two irrigation ports 636 (one above the planar distal portion and one below the planar distal portion) in communication with the lumen of tubular proximal portion 622. Width 632 is preferably between 0.03 and 0.2 inches, and more preferably between 0.04 and 0.1 inches. Thickness 630 is preferably less than 0.08 inches and more preferably less than 0.04 inches. Included angle 637 is preferably between 20 and 70 degrees, and more preferably between 40 and 60 degrees. Distal-most radius 639 is preferably between 0.003 and 0.03 inches, and more preferably between 0.006 and 0.02 inches.

While the shape of distal edge 638 is a wedge formed by linear edge portions, other shapes are anticipated in which wedge shape edge 638 is formed by curvilinear segments terminating at a distal radius 639.

Cutting and desiccation performance of an electrosurgical cutting device of the present invention may be strongly affected by the amount of exposed surface area in contact with the tissue during cutting, and in contact with the tissue and conductive irrigant during coagulation. Accordingly, it may be advantageous in certain circumstances to insulate a portion of the electrode distal to the irrigation ports so as to leave only a predetermined uninsulated region adjacent to the distal cutting edge of the electrode. When cutting, only the portion of the uninsulated region in contact with tissue will conduct current. When coagulating using conductive irrigant applied to the site, only portions of the uninsulated region in contact with the irrigant and/or tissue will conduct current.

Figure 49:
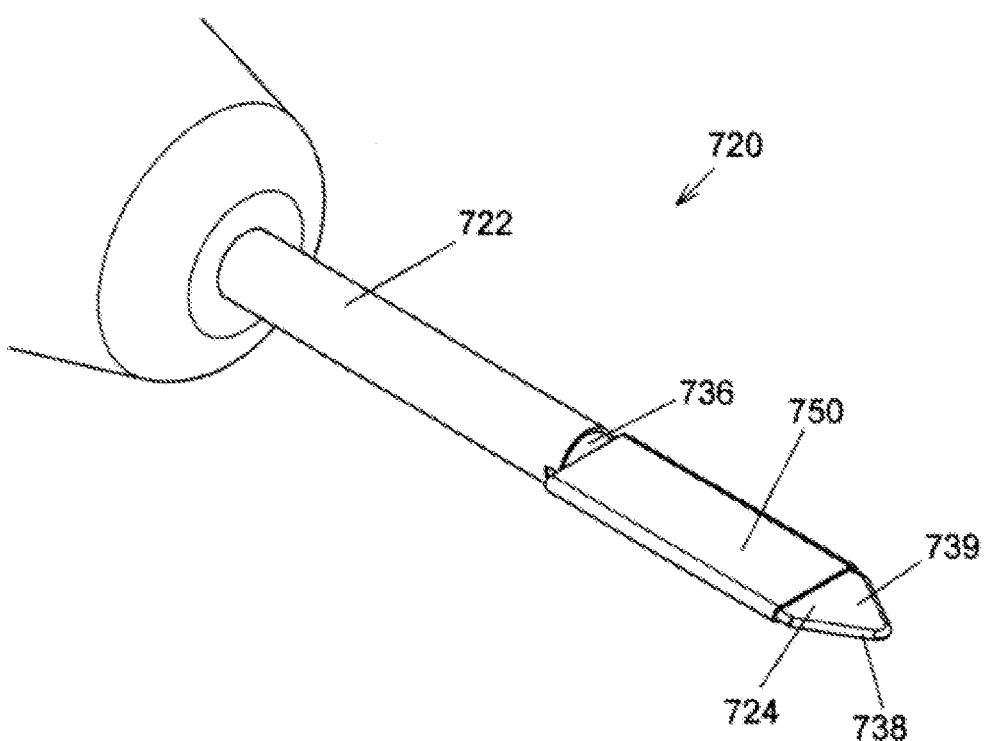
FIG. 49 is a perspective view of an alternate embodiment electrode of the instant invention.
Figure 50:
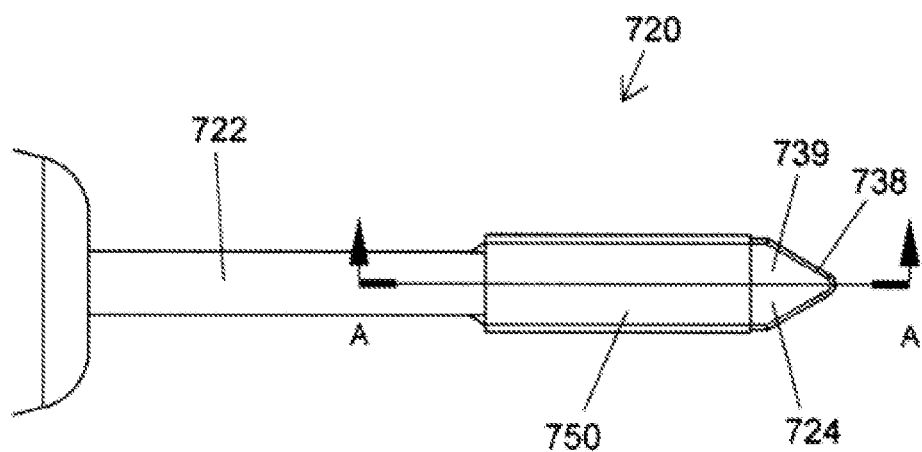
FIG. 50 is a plan view of the objects of FIG. 49.
Figure 51:
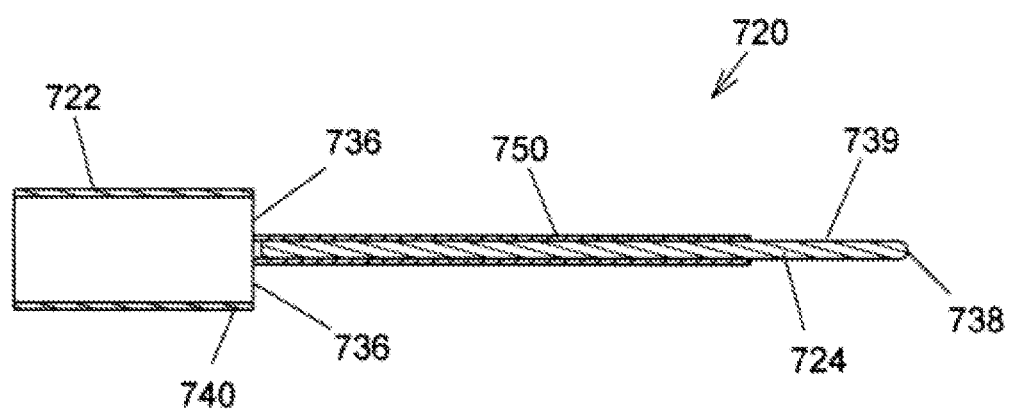
FIG. 51 is an expanded side elevational sectional view of the objects of FIG. 50 at location A-A.

FIGS. 49 through 51 depict alternate embodiment electrode 720 identical in all aspects except as indicated to electrode 620 (FIGS. 45 through 48). Electrode 720 has applied to its planar distal portion 724 distal to irrigation ports 736 dielectric coating 750 so as to leave uninsulated region 739 adjacent to distal cutting edge 738. In use only region 739 will conduct RF energy for cutting and coagulation.

Figure 52:
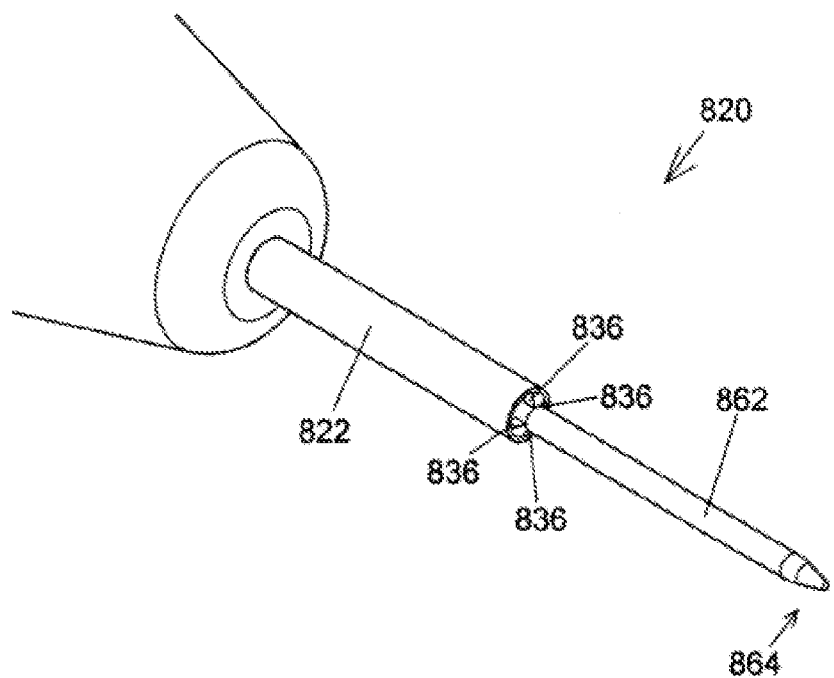
FIG. 52 is a perspective view of an alternate embodiment electrode of the instant invention.
Figure 53:
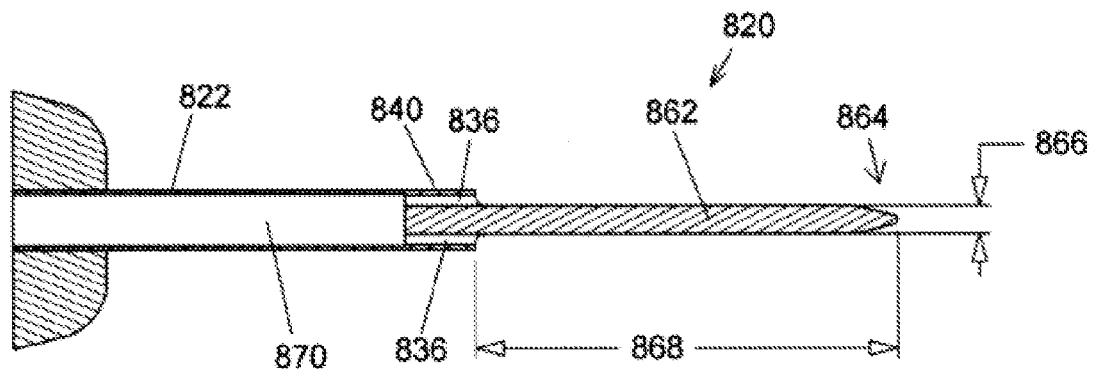
FIG. 53 is a side elevational sectional view of the objects of FIG. 52 along a center plane of the electrode.

Needle electrodes, small diameter cylindrical electrodes having a tapered distal end, are frequently used in electrosurgery for cutting tissue because the high current densities at the tapered distal end produce highly efficient cutting. An alternate embodiment of the present invention combines the efficient cutting ability of a needle electrode with enhanced coagulation performance through the on-demand application of conductive irrigant so as to reduce the current density when coagulating. Referring to FIGS. 52 and 53, electrode 820 has a proximal tubular portion 822 and an elongate cylindrical distal portion 862 of diameter 866 and length 868, portion 862 having a tapered distal end 864. A single irrigation port 836 at distal end 840 of tubular proximal portion 822 allows conductive irrigant to flow from lumen 870 of proximal portion 822 to the region surrounding distal portion 862. Electrode 820 may be of a unitary construction, or may be an assembly of elongate distal portion 862 affixed to distal end 840 of proximal portion 822 by means of welding, brazing or mechanical assembly. Diameter 866 is preferably between 0.01 and 0.12 inches and more preferably between 0.02 and 0.08 inches. Length 868 is preferably between 0.3 and 1.5 inches and more preferably between 0.5 and 1 inches. While electrode 820 has a single irrigation portion 836 for supplying irrigant to the region surrounding distal portion 862, other embodiments having multiple irrigation ports 836 are contemplated herein, with the number of irrigation ports 836 being determined by the intended use of the device 800.

Figure 54:
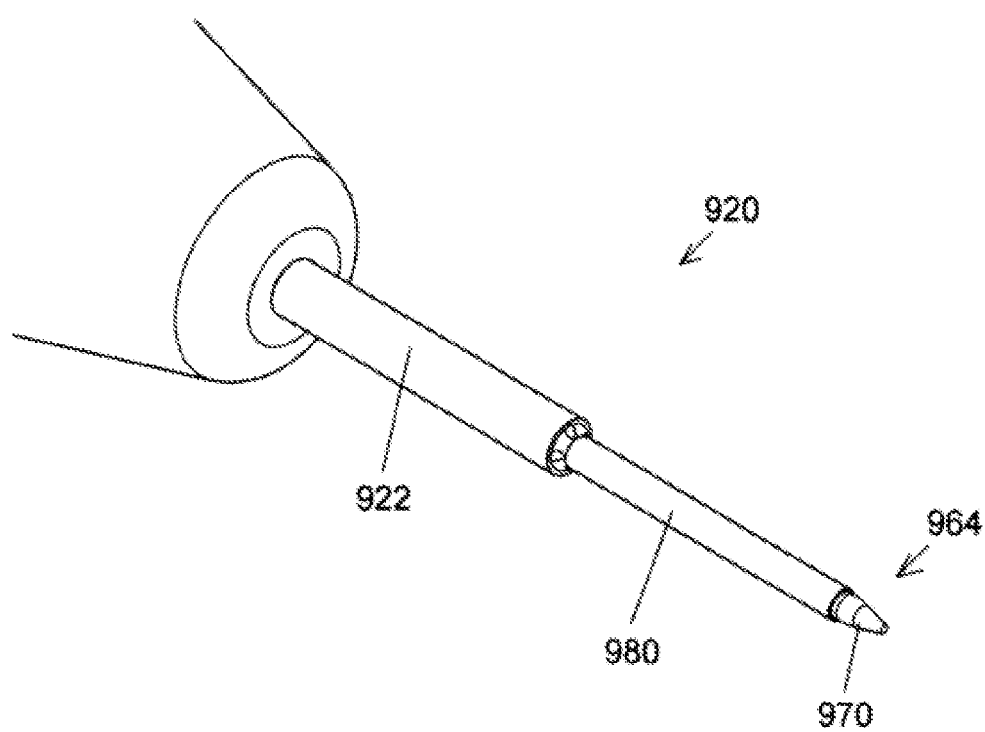
FIG. 54 is a perspective view of an alternate embodiment electrode of the instant invention.
Figure 55:
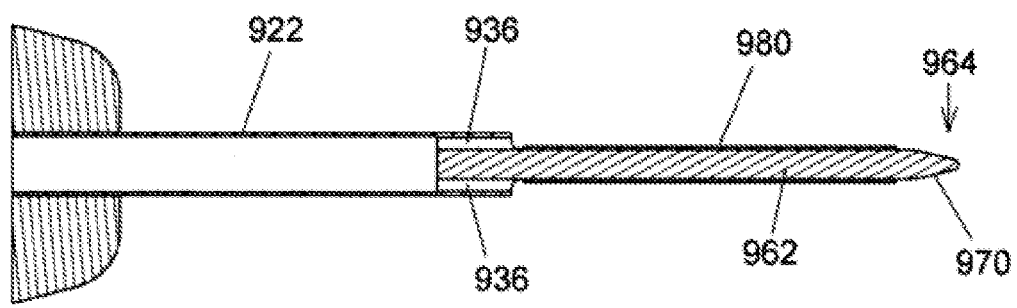
FIG. 55 is a side elevational sectional view of the objects of FIG. 54 along a center plane of the electrode.

The cutting efficiency of needle electrodes may be enhanced by insulating regions of the cylindrical distal portion proximal to the tapered distal tip. FIGS. 54 and 55 depict an alternate embodiment needle electrode 920 identical in form and function to electrode 820 except that dielectric coating 980 insulates elongate cylindrical distal portion 962 except for region 970 adjacent to tapered distal tip 964. When used in cutting mode, RF energy is conducted only from region 970 to tissue in contact with region 970. When used in coagulation monde RF energy is conducted only from region 970 to conductive irrigant and tissue in contact with region 970 thereby enhancing desiccation of surrounding tissue.

Figure 56:
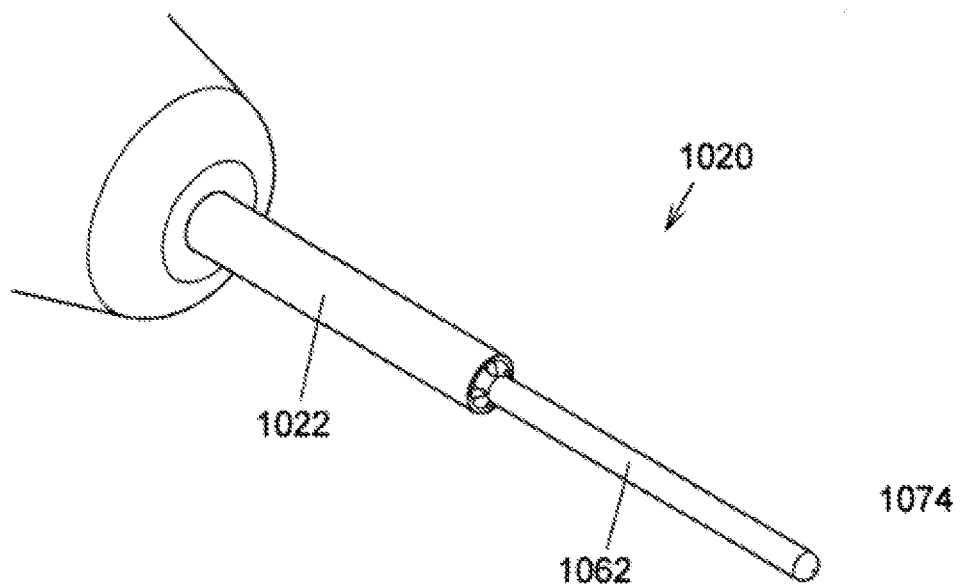
FIG. 56 is a perspective view of an alternate embodiment electrode of the instant invention.
Figure 57:
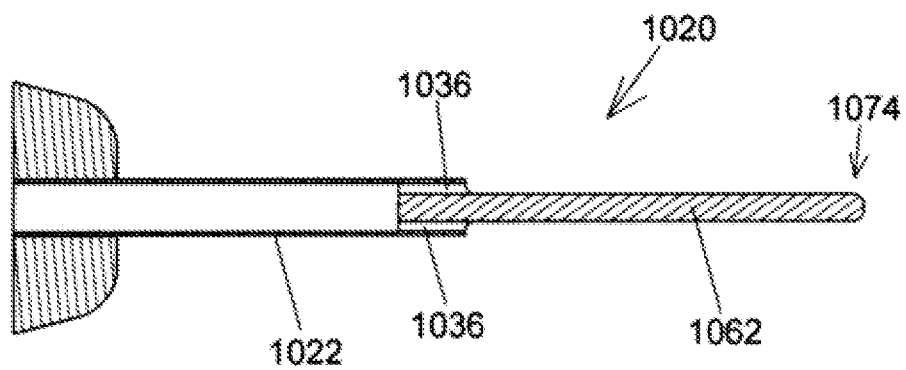
FIG. 57 is a side elevational sectional view of the objects of FIG. 56 along a center plane of the electrode.

The benefits of on-demand conductive irrigant delivery for enhanced desiccation may be realized with other configurations of active electrodes as well. FIGS. 56 and 57 depict active electrode 1020 identical in form and function to electrode 820 except that distal end 1074 of elongate portion 1062 of electrode 820 has a blunt, rounded shape. When provided with sufficient RF power, electrode 1020 is an effective tissue cutter, the density of the RF energy being sufficient to vaporize tissue that contacts electrode 1020. When used in coagulation mode with its associated locally delivered conductive irrigant, the blunt, rounded shape of distal end 1074 provides enhanced desiccation of tissue in its immediately surrounding region since increased power levels may be used without creating arcing and its associated vaporization of tissue.

Figure 58:
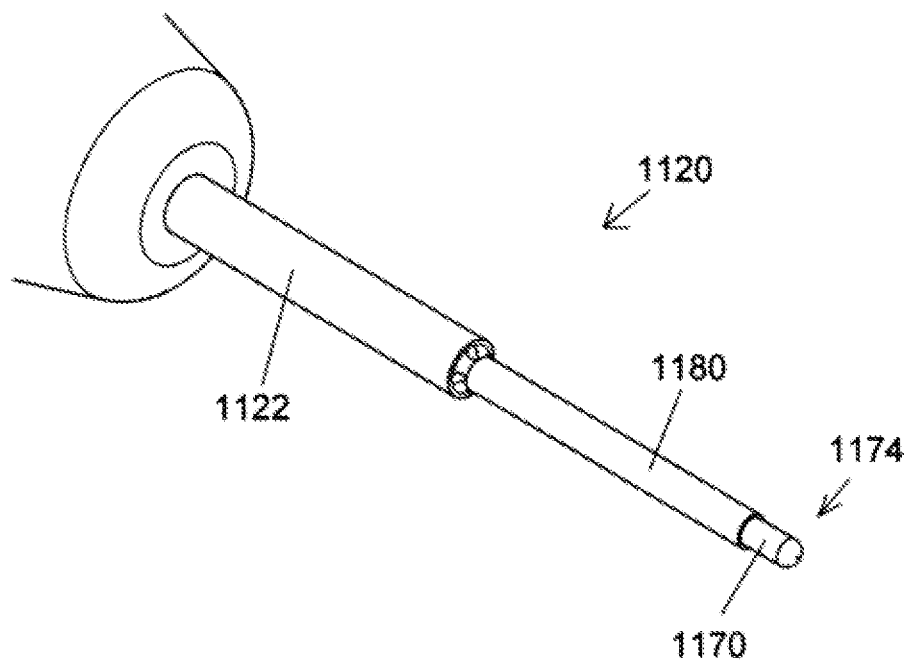
FIG. 58 is a perspective view of an alternate embodiment electrode of the instant invention.
Figure 59:
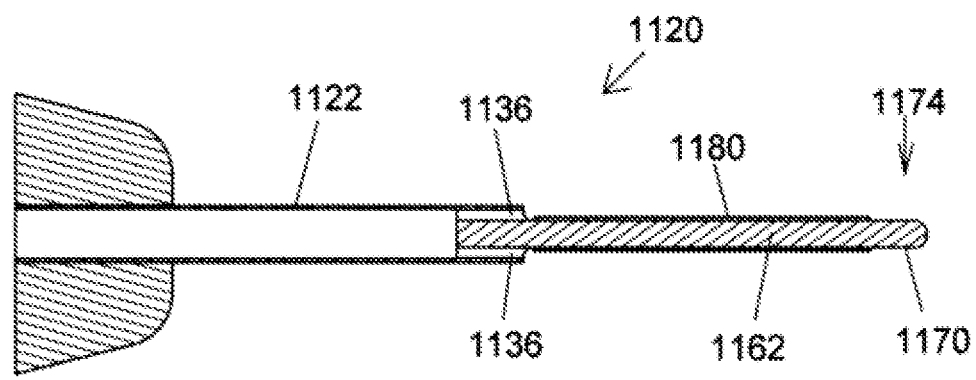
FIG. 59 is a side elevational sectional view of the objects of FIG. 58 along a center plane of the electrode.

As with electrodes 720 and 920, covering portions of electrode 1020 with a dielectric coating so as to localize the cutting and desiccating effects at the distal end of the electrode may be beneficial for certain uses. FIGS. 58 and 59 depict electrode 1120, which is identical to electrode 1020 in form and function except that dielectric coating 1180 covers the portion of elongate distal portion 1162 except for region 1170 at distal end 1174 of distal portion 1162. The length of uninsulated region 1170 may be increased or decreased depending on the application. Increasing the length of region 1170 may increase the maximum power required for effective tissue cutting, while decreasing the length of region 1170 may allow cutting and coagulation/desiccation at very low power levels.

Distal end 1174 of elongate distal portion 1162 is shown with a rounded, hemispherical shape. Other configurations may also be used. For instance, distal end 1174 may have a planar surface normal to the axis of electrode 1120, a shape wherein the sharp corners may cause concentration of the RF energy and enhanced vaporization. This effect may be intensified by providing grooves or protuberances on the planar surface so as to provide additional sharp edges. Conversely, if the edges created by the intersection of the planar surface and cylindrical surface are rounded the intensification of RF energy can be reduced so as to allow the use of increased power levels during coagulation for enhancement of the desiccating effect.

Indeed, any electrode shape may benefit from the on-demand delivery of conductive irrigant to the region surrounding the electrode to decrease current density for the purpose of enhanced tissue desiccation in accordance with the principles of the instant invention. These electrodes may have insulated regions so as to localize the cutting and desiccation action.

All patents and publications mentioned herein are incorporated by reference in their entirety. Nothing herein is to be construed as an admission that the invention is not entitled to antedate such disclosure by virtue of prior invention.

While the invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention.

Other advantages and features will become apparent from the claims filed hereafter, with the scope of such claims to be determined by their reasonable equivalents, as would be understood by those skilled in the art. Thus, the invention is intended to be defined not by the above description, but by the following claims and their equivalents.

What is claimed:

1. A method of performing an electrosurgical procedure on a living subject in which target tissue of interest within a surgical site is treated, said method comprising the steps of:
   a. introducing a dual-mode electrosurgical device into the subject, wherein said dual-mode electrosurgical device comprises a distal end active electrode characterized by (i) a tubular proximal portion, a distal end of which includes at least one irrigation port configured to introduce a conductive irrigant to the surgical site and (ii) an elongate distal portion that extends from the distal end of said tubular proximal portion and thereby defines said at least one irrigation port,
   b. manipulating said device to the surgical site;
   c. using said dual-mode electrosurgical device to apply a low density RF energy to said surgical site so as to desiccate tissue and produce hemostasis at said site, wherein said conductive irrigant is supplied on command to the surgical site via said at least one irrigation port during or prior to the application of said low density RF so as to reduce the effective current density and thus produce desiccation of tissue in contact with said conductive irrigant; and d. using said dual-mode electrosurgical device to apply a higher-density RF energy to tissue at said surgical site so as to cut or vaporize said tissue either before or after the performance of step (c).

2. The method of claim 1, wherein said elongate distal portion has a closed distal end.

3. The method of claim 1, wherein said elongate distal portion is affixed to the distal end of said tubular proximal portion by means of welding, brazing or mechanical assembly.

4. The method of claim 1, wherein said elongate distal portion and said tubular proximal portion are of unitary construction.

5. The method of claim 1, wherein said elongate distal portion retracts into said tubular proximal portion.

6. The method of claim 1, wherein said elongate distal portion comprises a distal tip that is provided with serrations to enhance cutting performance.

7. The method of claim 1, wherein said distal end active electrode further comprises (iii) an insulating dielectric coating disposed over only a proximal section of said elongate distal portion such that a distal section is uninsulated.

8. The method of claim 1, wherein the elongate distal portion comprises a flattened blade element having a top side and a bottom side, further wherein said tubular proximal portion comprises a first irrigation port proximate to said blade element top side and an opposed second irrigation port proximate to said blade element bottom side.

9. The method of claim 8, wherein said active electrode is fabricated from a piece of metal tubing having proximal and distal portions, wherein the proximal portion of said metal tubing has a diameter equivalent to that of the tubular proximal portion of said active electrode and the distal portion of said metal tubing is flattened to form the blade element of said active electrode.

10. The method of claim 8, wherein said flattened blade element has a distal-most cutting edge.

11. The method of claim 10, wherein said distal-most cutting edge is wedge shaped.

12. The method of claim 1, wherein the elongate distal portion comprises a cylindrical element.

13. The method of claim 12, wherein said cylindrical element has a sharpened tapered distal tip.

14. The method of claim 12, wherein a distal end of said cylindrical element has a blunt rounded or hemispherical shape.

15. The method of claim 12, wherein a distal end of said cylindrical element comprises a planar surface normal to a longitudinal axis of the electrode.

16. The method of claim 15, wherein said normal planar surface further comprises grooves or protuberances.

17. The method of claim 1, wherein said conductive irrigant is supplied to the device by one of: gravity from a hung bag, a manual pump activated by a surgeon, and a mechanical pump.

18. The method of claim 1, wherein said conductive irrigant is supplied to the surgical site upon manual action or electrical activation by a surgeon.

19. The method of claim 1, wherein the electrosurgical procedure comprises a surgical procedure selected from the group consisting of tonsillectomy, liver resection, breast augmentation, breast reduction, breast mastopexy, and abdominoplasty.

20. The method of claim 1, wherein step (d) is performed in the absence of conductive irrigant whereas step (c) is performed in the presence of conductive irrigant.

* * * * *